(12) United States Patent
Aojula et al.

(10) Patent No.: US 7,838,218 B2
(45) Date of Patent: Nov. 23, 2010

(54) LIGHT EMITTING PROBES

(76) Inventors: Harmesh Singh Aojula, AnMat Technology Limited, Saddleworth Business Centre, Huddersfield Road, Delph, Oldham (GB) OL3 5DF; David John Clarke, AnMat Technology Limited, Saddleworth Business Centre, Huddersfield Road, Delph, Oldham (GB) OL3 5DF; Shaun Clive Offerman, AnMat Technology Limited, Saddleworth Business Centre, Huddersfield Road, Delph, Oldham (GB) OL3 5DF ( * ) Notice: Subject to any disclaimer, the term of this patent is extended or adjusted under 35 U.S.C. 154(b) by 552 days.

(21) Appl. No.: 10/558,327

(22) PCT Filed: May 24, 2004

(86) PCT No.: PCT/GB2004/002218

§ 371 (c)(1),
(2), (4) Date: Nov. 6, 2006

(87) PCT Pub. No.: WO2004/104594

PCT Pub. Date: Dec. 2, 2004

(65) Prior Publication Data

US 2007/0202498 A1    Aug. 30, 2007

(30) Foreign Application Priority Data

May 23, 2003    (GB) .................................. 0311948.4

(51) Int. Cl.
*C12Q 1/68*     (2006.01)
*G01N 33/55*   (2006.01)
*C07H 21/02*   (2006.01)
*C07H 21/04*   (2006.01)
*C07K 14/00*   (2006.01)

(52) U.S. Cl. ........................... 435/6; 435/7.1; 536/23.1; 536/24.3; 530/350

(58) Field of Classification Search ..................... 435/6, 435/7.1; 536/23.1, 24.3; 530/350
See application file for complete search history.

(56) References Cited

U.S. PATENT DOCUMENTS

| | | | | |
|---|---|---|---|---|
| 5,314,802 | A * | 5/1994 | Kidwell ...................... | 435/7.1 |
| 5,332,659 | A * | 7/1994 | Kidwell ......................... | 435/6 |
| 5,998,146 | A * | 12/1999 | Latva et al. ..................... | 435/6 |
| 6,500,622 | B2 * | 12/2002 | Bruchez et al. ................ | 435/6 |
| 7,081,336 | B2 * | 7/2006 | Bao et al. ....................... | 435/6 |
| 2003/0175728 | A1 * | 9/2003 | Belousov et al. ............... | 435/6 |

(Continued)

FOREIGN PATENT DOCUMENTS

EP    0229943    *    7/1989

(Continued)

OTHER PUBLICATIONS

Packard et al., Characterization of fluorescence quenching in bifluorophoric protease substrates. Biophysical Chemistry 67 : 167-176 (1997).*

(Continued)

*Primary Examiner*—Ethan Whisenant
(74) *Attorney, Agent, or Firm*—Duncan Palamatier

(57) ABSTRACT

This invention relates to a composition comprising at least two chemically different fluorophores, providing a donor and an acceptor respectively, connected together by at least one linker moiety and bonded to a binder moiety.

3 Claims, 14 Drawing Sheets

U.S. PATENT DOCUMENTS

| | | | |
|---|---|---|---|
| 2005/0123957 A1* | 6/2005 | Laitala | 435/6 |
| 2006/0115842 A1* | 6/2006 | Laitala | 435/6 |
| 2006/0228725 A1* | 10/2006 | Salafsky | 435/6 |
| 2007/0202498 A1* | 8/2007 | Aojula et al. | 435/6 |

FOREIGN PATENT DOCUMENTS

| | | | |
|---|---|---|---|
| EP | 1264897 A | * | 12/2002 |
| WO | WO96/30540 A2 | * | 10/1996 |
| WO | WO00/11446 A2 | * | 3/2000 |
| WO | WO01/18238 A1 | * | 3/2001 |

OTHER PUBLICATIONS

Tyagi et al., Wavelength-shifting molecular beacons Nature Biotechnology 18 : 1191-1196 (2000).*

Tyagi et al., Molecular Beacons: Probes that fluoresce upon Hybridization. Nature Biotechnology 14 :303-308 (Mar. 1996).*

Ahn et al. Analytical Biochemistry 306 : 247-251 (2002).*

Marek et al. Bioconjugate Chemistry 8 : 560-566 (1997).*

Muller et al., Chemistry and Physics of lipids. 106 :89-99 (2000).*

Packard et al., Biophysical Chemistry 67 : 167-176 (1997).*

Song et al. Langmuir 15 : 4710-4712 (1999).*

Ashikawa et al., J. of Biochemisrty 92 : 1425-1430 (1982).*

Pohl et al., Analytical Biochemistry 165 : 96-101 (1987).*

Ruud Hovius, et al., "Fluorescence techniques: shedding light on ligand-receptor interactions", TiPS, Jul. 2000 (vol. 21), pp. 266-273.

Robert M. Clegg, "Fluorescence resonance energy transfer", Current Opinion in Biotechnology 1995, 6:103-110.

* cited by examiner (b)

(a)

(b)

(a)

(b)

(a)

(b)

(a)

(b)

(a)

(b)

SEQUENCE LISTING

```
<160> NUMBER OF SEQ ID NOS: 7

<210> SEQ ID NO 1
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Acylated on N-terminal with
      N-(1-pyrenebutanoyl) Beta alanine
<220> FEATURE:
<221> NAME/KEY: MISC_FEATURE
<222> LOCATION: (7)..(7)
<223> OTHER INFORMATION: Amidated on C-terminal and branched off from
      Lysyl epsilon amino with Fluorescein isothiocyanate labelled Beta
      Alanine

<400> SEQUENCE: 1

Ala Leu Glu Gln Lys His Lys
1               5

<210> SEQ ID NO 2
<211> LENGTH: 7
<212> TYPE: PRT
```

```
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acylated on N-terminal with
      N-(1-pyrenebutanoyl) Beta alanine
<220> FEATURE:
<221> NAME/KEY: MISC_FEATURE
<222> LOCATION: (5)..(5)
<223> OTHER INFORMATION: Biotinylated
<220> FEATURE:
<221> NAME/KEY: MISC_FEATURE
<222> LOCATION: (7)..(7)
<223> OTHER INFORMATION: Amidated on C-terminal and branched off from
      Lysyl epsilon amino with Fluorescein isothiocyanate labelled Beta
      Alanine

<400> SEQUENCE: 2

Ala Leu Glu Gln Lys His Lys
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acylated on N-terminal with
      N-(1-pyrenebutanoyl) Beta alanine
<220> FEATURE:
<221> NAME/KEY: MISC_FEATURE
<222> LOCATION: (8)..(8)
<223> OTHER INFORMATION: Amidated on C-terminal and branched off from
      Lysyl epsilon amino with Fluorescein isothiocyanate labelled Beta
      Alanine

<400> SEQUENCE: 3

Gly Ala Leu Glu Gln Lys His Lys
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acylated on N-terminal with
      N-(1-pyrenebutanoyl) Beta alanine
<220> FEATURE:
<221> NAME/KEY: MISC_FEATURE
<222> LOCATION: (9)..(9)
<223> OTHER INFORMATION: Amidated on C-terminal and branched off from
      Lysyl epsilon amino with Fluorescein isothiocyanate labelled Beta
      Alanine

<400> SEQUENCE: 4

Gly Gly Ala Leu Glu Gln Lys His Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (1)..(1)
<223> OTHER INFORMATION: Acylated on N-terminal with Beta alanine
<220> FEATURE:
<221> NAME/KEY: MISC_FEATURE
<222> LOCATION: (7)..(7)
<223> OTHER INFORMATION: Amidated on C-terminal and branched off from
      Lysyl epsilon amino with Fluorescein isothiocyanate labelled Beta
      Alanine

<400> SEQUENCE: 5

Ala Leu Glu Gln Lys His Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Acylated on N-terminal with
      N-(1-pyrenebutanoyl) Beta alanine
<220> FEATURE:
<221> NAME/KEY: MISC_FEATURE
<222> LOCATION: (7)..(7)
<223> OTHER INFORMATION: Amidated on C-terminal and branched off from
      Lysyl epsilon amino with Beta Alanine

<400> SEQUENCE: 6

Ala Leu Glu Gln Lys His Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Acylated on N-terminal with Beta alanine
<220> FEATURE:
<221> NAME/KEY: MISC_FEATURE
<222> LOCATION: (7)..(7)
<223> OTHER INFORMATION: Amidated on C-terminal and branched off
      sequence from Lysyl residue with Beta alanine

<400> SEQUENCE: 7

Ala Leu Glu Gln Lys His Lys
1               5
```

LIGHT EMITTING PROBES

FIELD TO WHICH THE INVENTION RELATES

The present invention relates to the field of fluorescence and to novel multiple fluorophore compositions which are bonded to binder molecules to give fluorescence enhancement. The invention also relates to obtaining fluorescence enhancement by energy transfer enabled with binder molecules in diagnostic applications.

BACKGROUND

Fluorescence occurs in certain molecules called fluorophores or fluorescent dyes in three sequential stages involving excitation, excited state lifetime, and fluorescence emission. When an excited fluorophore is raised to a singlet state, it decays back to ground state by emission of a photon that generates a fluorescent signal. Generally, fluorescent dyes absorb light at a particular wavelength and emit light at a wavelength longer than that absorbed. The difference between the absorption and emission wavelength maxima is known as the Stokes shift (Handbook of Fluorescent Probes and Research Products, Molecular Probes, Eugene, Oreg., Haughland, 2002). Large Stokes shifts and fluorescence emission at long wavelengths are viewed as practically useful to overcome the problem of fluorescence measurement in the presence of background signals such as, Raman scattering and auto fluorescence (e.g. of plastic and biological materials). Only a very few individual fluorescent dyes have large Stokes shifts. However, large Stokes shifts can result from fluorescent dye pairs. In the presence of other molecules, including dyes, the fluorescence of most fluorophores is typically quenched, whereas in some cases, fluorescence at longer wavelengths may result. Three different types of such fluorescence from dye pairs have been described.

Excimers and exciplexes are electronically excited dimer complexes which are non-binding in the ground state. Excimers and exciplexes complexes can be formed between dye molecules, whose close proximity is typically less than a few nm. The formation of such complexes effectively results in fluorescence with a large Stokes shift J. Phys. Chem., 100, (1996)11539-11545. In the case of excimers, a pair of dye molecules form a complex by the interaction of an excited molecular entity with a ground state partner of the same structure. The close proximity between such molecules results in energy transfer and fluorescence with a large Stokes shift. In the case of exciplexes, a pair of dye molecules (sometimes only one being a fluorescent dye) form a complex between an excited molecular entity with a ground state partner of a different chemical structure. The molecules are in very close proximity to transfer energy. The close proximity affects fluorescence properties. For instance at high concentrations, or when linked on a short spacer, two pyrene molecules are in the vicinity of each other for the π-systems to overlap causing a fluorescence emission maximum at a longer wavelength (about 470 nm) than at low concentrations where the pyrene molecules are too far apart as monomers and only an emission at 378 and 396 nm is observed.

Fluorescence resonance energy transfer (FRET) is a technique in which the energy emitted from one fluorophore (the donor) causes the excitation of a second, longer wavelength, fluorophore (the acceptor). The transfer of the excitation energy of the donor to the acceptor molecule is only possible if the electronic transition of the donor from the excited state to the ground state corresponds to the absorption wavelength of the acceptor. This requires substantial overlap of the fluorescence emission spectrum of the donor and the absorption spectrum of the acceptor molecule. The combination of fluorophores to form FRET pairs is limited by the requirement for the donor's emission spectra to overlap with acceptor's excitation spectra. In addition to this, the transition dipoles of donor and acceptor need to be correctly orientated. (Matyus, 1992, J. Photochem. Photobiol. B: Biol., 12: 323-337). In contrast to excimers and exciplex fluorescence, FRET pairs do not require the dye molecules forming the complexes to be in very close proximity as FRET can arise at up to 10 nm distance although typically the range is 4-6 nm for favourable pairs of donor and acceptor dyes. FRET is commonly used in several detection modes to measure or identify a variety of biologically active molecules including nucleic acids, oligonucleotides, and proteins. One of the advantages of FRET is that fluorescence arises under physiological conditions in comparison to exciplex fluorescence which is typically weak under aqueous conditions, requiring the addition of organic solvents or formation in a similar molecular microenvironment.

A fluorescent chemosensor modulates its emission properties upon binding of an analyte to a receptor. Fluorescence properties have been used to provide information on ligand binding, ligand or probe environment, and conformational changes. A number of homogeneous assay systems, which use fluorescence as detection means are based on polarization, lifetimes, quenching, and energy transfer schemes (Drug Discovery Today (2003) Vol. 8, No. 22 1035-1043).

Peptides doubly tagged with fluorescent dyes (Biophys. Chem. 67(1997), 167-176) have previously been used as fluorogenic substrates for proteinases. In these assays dye-to-dye contact diminishes the fluorescence of the participating dyes by quenching. On enzymatic cleavage of the peptide link, the dye-tagged products dissociate, breaking dye to dye contact, thus relieving quenching of the fluorescence. To observe the increase in fluorescence indicative of enzyme activity usually requires breaking of a covalent bond in the linker. Fluorescent quenching has been used (Analytical Biochemistry 165(1987) 96-101) to measure the distance between a quencher and a fluorophore when attached to a peptide linker. Ai-Ping Wei et al (WO95/03429) uses antibody-antigen reaction to break dye-to-dye contact in order that molecules in the dimer state (fluorescence quenched) become monomeric (fluorescence unquenched) to relieve quenching. This was used to form assays measuring specific antibodies to a recognized peptidic epitope that linked the two dyes. In common with many other homogeneous dequenching assays, while this method can measure antibodies specific to the epitope (used to bind the dyes) in a noncompetitive manner, its adaptation to measuring other analytes, possible only in competitive mode, suffers from disadvantage in that the fluorescence signal becomes indirectly proportional to analyte concentration.

Pyrenyl derivatized peptides have been successfully used to investigate peptidic structures (Org. Lett, Vol. 3, No. 16, 2001). When pyrenes are separated as monomers, chromophores display an emission band with distinct vibrational structure between 370 and 430 nm; a broad vibrationless (excimer) band centered around 470 nm is observed when pyrenes are in close proximity. In addition, the ground-state aggregation of the chromophores leads to perturbation in the UV/vis absorption. An assay using fluorogenic peptides based on the monomer/excimer (Analytical Biochemistry 306(2002), 247-251) fluorescence features of pyrene was developed to measure the proteolytic activity of trypsin. Two pyrene moieties incorporated into the respective N- and C-terminus of the peptides led to an expected increase in monomer fluorescence and a decrease in excimer fluorescence of pyrene as the peptide is hydrolysed by the enzyme. In another assay (Bioconjug Chem. (1997) 8, 560-6) streptavidin binding to a biotin labeled pyrene derivative causes the appearance of the excimer emitting at 470 nm. The ratio of monomer to excimer then provides the concentration of unlabeled biotin in the sample. Without the streptavidin present, only the monomer emitting at 378 and 390 nm is observed. In yet another assay system (U.S. Pat. No. 5,314,802) the excimer can be formed by assembling two pyrenes in close proximity using an antibody and this was used in a competitive manner with analyte modified pyrene analogues to measure free analyte. Pyrene excimer has also been used in FRET assays where the energy transfer from the excimer emission (470 nm) to BODIPY-FL-GM1 was anticipated by the good overlap between pyrene excimer fluorescence and absorption spectrum of BODIPY-FL-GM1 in lipid vesicles (Langmuir 1999, 15, 4710-4712). By using pyrene-containing lipids, the intensity of the excimer peak has been used to report lipid redistribution in liposomes (Chem. Phys. Lipids 2000, 106, 89-99). Pyrene is a hydrophobic molecule whose fluorescence efficiency is susceptible to solvent polarity. The fluorescence lifetime of pyrene is significantly longer and this property has been used in number of studies (Journal of Biochemistry (1982) Vol 92, 1425-1430) to probe microenvironment. Both pyrene monomer and excimer fluorescence has been used (Nucleic Acids Res. 26(1998), 5409-5416, U.S. Pat. No. 5,332,659) as an indicator for monitoring DNA hybridisation. Hybridisation of two oligonucleotides labelled by a single pyrene group at the terminal ends with complementary DNA results in the excimer formation.

Molecular Beacons (Nature Biotechnology 14 (1996), pp. 303-308) contain a fluorophore and a quencher linked in a stem-loop structure. The stem sequence maintains dyes in close proximity so that photons emitted by the fluorophore are quenched and not emitted. The loop sequence hybridises with the target giving the spatial separation of the fluorophore from the quencher, allowing the fluorescence to appear and be measured. HyBeacons (International Patent Application No. PCT/GB01/01430) uses a single probe, in the absence of a quencher moiety, enhancing fluorescence when bound to complementary target DNA sequences than when the probes are in the single-stranded conformation. This shift in the quantity of fluorescence emission occurs as a direct result of target hybridization permitting the detection of DNA sequences.

SUMMARY OF THE INVENTION

According to a first aspect, the present invention provides a composition comprising at least two chemically different fluorophores, providing a donor and an acceptor respectively, connected together by at least one linker moiety and bonded to a binder moiety.

The fluorescent emission band of one fluorophore (donor) may have little or no overlap with the absorption band of another fluorophore (acceptor) in the composition. In this case, any fluorescence observed would be due to individual fluorescence of the fluorophore molecules. According to the present invention, the bonding of the composition to a binder moiety results in an increase in fluorescence due to efficient energy transfer between the different fluorophores. The extent of the overlap between the emission band of at least one donor fluorophore and the absorption band of at least one acceptor fluorophore may be independent from the intensity of fluorescence emitted from the composition.

The excitation of the fluorophores is preferably by photons from a light source.

The fluorescence emission intensity of the acceptor may be enhanced without significantly affecting the spectral overlap. Preferably, the acceptor fluorescence is enhanced at least two-fold.

An important feature of this invention is that the energy transfer may be observed with the concurrent fluorescence of the donor. In other methods such as FRET, the donor fluorescence is lost or reduced at the expense of a rise in the acceptor fluorescence. In the present invention both the donor and acceptor emission may be enhanced although by different levels. Preferably the emission of acceptor fluorophore is increased more than donor fluorophore.

The invention is distinguished from exciplex or excimers complexes since excitation of the donor results in neither exciplex nor excimer emission. There is no evidence of excimer or exciplex fluorescence apparent from fluorescence emission spectra of these assemblies.

Preferably, fluorophores efficiently produce fluorescence upon excitation with light which has a wavelength in the range of about 200 to about 1000 nanometers, preferably in the range of about 600 to 800 nanometers.

Compositions according to this invention may be excited at wavelengths not possible by other methods. These wavelengths may be shorter than the normal absorption wavelength band of the emitting fluorophore when not in a composition according to this invention.

Accordingly, there are many fluorophores which may be used.

Types of fluorophores are listed below by way of example only:

aromatic hydrocarbons such as naphthalene, biphenyl, fluorene, acenaphthene, anthracene, phenanthrene, chrysene, coronene, fluoranthene, pyrene, perylene, triphenylene, 9-cyanoanthracene, 9,10-dicyanoanthracene; azine dyes such as lumiflavin, riboflavin; coumarin dyes such as coumarylpyrone; xanthene dyes such as fluorescein, fluorescein, isothiocyanate, rhodamine B, rhodamine 6G, cyanine dyes, stilbene derivatives, oxazole, and oxadiazole derivatives; phthalocyanines, macrocycles such as derivatives of porphyrins, azaporphyrins, corrins, sapphyrins and porphycenes and other like macrocycles having conjugated .pi.-electron ring systems., bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, and fluorescent europium and terbium complexes and related compounds. Other inorganic fluorophores such the fluorescent semiconductor quantum dots can also be employed.

Many more fluorophores including Alexa fluor dyes with various excitation and emission wavelengths are reported in Handbook of Fluorescent Probes and Research Products, Molecular Probes, Eugene, Oreg., Haughland, 2002, and may be used to form pairs which will not have overlapping emission and absorption spectra. In view of the above, it is understood that a variety of donor fluorophore/acceptor pairs may be considered to be atypical or non FRET pairs. Preferably, the acceptor fluorophore has no or minimal spectral overlap with the first donor. Preferably, the excitation wavelength maximum for the acceptor is at least 60 nm longer than the donor excitation wavelength maximum. Preferably, the donor's emission maximum is at least 30 nm shorter than excitation maximum of acceptor. By way of example, the donor fluorophore pyrene may be used in combination with acceptor fluorescein, texas red or eosin. Other fluorophores may also be use as donors or acceptors, for example, a lanthanide atom, also known as a rare-earth element. Lanthanides such as terbium (Tb), europium (Eu), dysprosium (Dy) and samarium (Sm) with long lifetimes. Naturally present fluorophores can also be used for instance tryptophan. Fluorophores may be used in multiples. For example tryptophan can transfer energy to pyrene as these are standard FRET pairs and pyrene could then in turn transfer energy to FITC.

The composition may comprise multiple donor or acceptor fluorophores. In particular, the compositions may comprise double or triple donor and/or acceptor fluorophores.

For example, the three-fluorophore systems may comprise donor/acceptor pairs that share a common fluorophore. Compositions may comprise two parallel energy transfers from a single donor to two different acceptors. The arrangement of such multicomponent systems on a linker are known J. Am. Chem. Soc. 2003, 125, 7336-7343; Chem. Commun. 2000, 1043-1044. Such designed systems with multi-step energy transfers may be used as biomimetic photosynthetic reaction centers and in multiplex assays. The systems offer several advantages over one-step transfer such as higher efficiency of long-range transfer, larger Stokes shift, and better detection sensitivity for acceptor fluorescence.

The composition may further comprise a ligand moiety. The ligand moiety may be a hapten. Preferably, the ligand moiety binds to the linker moiety Preferably, at least one fluorophore is a polyaromatic hydrocarbon. At least one fluorophore may be a hetrocyclic compound. Preferably, the donor fluorophore is selected from pyrene, naphthalene, perylene, coronene or porphyrin. The acceptor fluorophore is preferably selected from acridine orange, Edans, Eosin, Erythrosin, Oregon Green, cyanines, fluorescein, FAM, rhodamine, TET, JOE, HEX, TAMRA, phycoerythrin, phycocyanin, anthracene ring, allophycocyanin, π-phthaldehyde label, fluorescamine, tetramethylrhodamine, BODIPY,ROX, Texas red and xanthines. Such groups are reported in the Handbook of Fluorescent Probes and Research Products, Molecular Probes, Eugene, Oreg., Haughland, 2002.

Fluorophores not known to normally transfer energy (e.g. by FRET or other methods) become able to transfer energy. Of course, according to this invention, fluorophores normally able to transfer energy by FRET may also be constructed into assemblies with other fluorophores not normally able to transfer energy and in this way the invention can be used in combination with FRET.

In a simple case of distinguishing this invention from FRET, two different fluorophores are connected by a linker to form a bis-fluorophore, where the two fluorophores are not or are atypical FRET dye pairs or are juxtaposed by the linker so that FRET is prevented. In the absence of binder, only the fluorescence of the individual fluorophore is discernible when excited at their respective absorption wavelengths. The linked fluorophores are then assembled using a binder causing the acceptor fluorophores to emit light when illuminated by the wavelength of excitation suited to the absorption or excitation of the donor fluorophores.

A suitable binder moiety may be any reagent which can modify the fluorescence spectrum or intensity of least one of the fluorophores. The fluorescence spectrum or intensity of the donor fluorophore may be modified. The fluorophore may be free dye to assess a potential binder.

Preferentially, a good binder moiety is indicated by its property to increase the fluorescence intensity. The binder moiety may be covalently bonded to the composition to provide further stabilization, however, the bonding of the binder preferably involves a non-covalent interaction. In the case where the binder is non-covalently bonded to the composition the maximum distance between the fluorophores remains unchanged as no covalent bonds are broken or formed. Non covalent forces may involve electrostatic forces, hydrogen bonding, Van der Waals forces, dipole-dipole interactions, and/or hydrophobic interactions. Further stabilisation of the binder with test probes may be made by covalent linkages.

The binder moiety is preferably selected from a polypeptide structure defining a hydrophobic cavity such as leucine, tryptophan, tyrosine or phenylalanine, apoproteins, albumins, rabbit serum, antibodies, receptors, polymers, solvents, albumin, liposome, micelle, oligonucleotide, nucleic acid, biomolecule, cyclodextrins and avidin. Solvents can be used as binders if they increase the acceptor fluorescence when donor is excited in accordance with the invention. Both polar solvents such as water and alcohols and non-polar solvents such as hydrocarbons may be used. A mixed solvent system may also be suitable. Additives that may provide a localised region of different hydrophobicity than the bulk phase of the medium containing sample could be used.

The linker moiety is preferably βAla-Ala-Leu-Glu-Gln-Lys-His-Lys(βAla)-amide. The linker moiety may be selected from peptides, spacers, alkyls, fatty acids, flexible molecules, polyethylene oxides, polyamino acids, polyamides, water soluble molecules and biomolecules.

The linker may be a biomolecule such as peptide, protein, carbohydrate, lipid, fatty acid, nucleic acid, DNA or a synthetic compound such as 1,6-diamnohexane, caproic acid polyglycine, polyaminoacid, —NHCH2—, —NHCH2CH2—, NHCH2CH2CH2—, polyethylene glycol and polymers. Heterofunctional, homofunctional reagents may be used in the linking reaction. Linkers which may be used are also given in Pierce Bio-Research Products Technical Bulletin, "Double-Agents", Bifunctional Crosslinking Reagents, Pierce Chemical Co., Rockford, Ill., U.S.A., 1982, Vol. 3. Further examples are in Kricka, J. J.; Ligand-Binder Assays; Labels and Analytical Strategies; pages 15-51; Marcel Dekker, Inc., New York, N.Y. (1985).

Haptens, ligands, analytes, enzyme cleavable bonds may already be present as part of the linker. Alternatively the linker may have one or more functional groups which may be employed as the site for attaching the hapten or ligand group. For the most part, linkers contain functional groups such as amines, amides, carboxyls, sulphydryls, hydroxyls, aldehydes, and/or others, to which an hapten with its own appropriate functional groups could be attached directly or indirectly. For example, test probes 1 to 5 have lysyl or glutamic acid residues which could be used in cross linking. Conditions for covalently attaching a hapten or ligand, including its derivatives and analogs, to a linker depend upon the particular molecular structure of both types of molecules. The attachment chemistry may vary depending upon the functional groups involved, the number of haptens or ligand molecules to be bonded and the desirability of including a spacer arm between the ligand and the linker. The composition must retain the ability to associate with the binder and to alter fluorescence intensity of acceptor fluorophore when donor is excited.

A ligand or hapten may be any type of molecule such as a peptide, polypeptide, protein, oligonucleic acid, polynucleic acid, carbohydrate, lipid, or any organic compound.

In the case of measuring analytes which compete with one of the fluorophores preferably the donor, for binding to receptor no further modifications may be necessary to structure. In such cases the fluorophore is considered as the ligand or hapten. Polyaromatic hydrocarbon fluorophores are preferable for such uses.

Fluorescence may arise from the assembly despite the emission of one fluorophore not falling within the absorption band of another dye, distinguishing the fluorescence from FRET. This invention is also distinguished from FRET in that efficient energy transfer only arises when the fluorophores form an assembly with binder.

In initial important demonstration of the invention, and also its use in the form a homogeneous fluorescent assay, we disclose fluorescent probes joined by linker, which are not normally expected to show energy transfer as the absorption spectra of the acceptor, and emission spectra of donor do not overlap significantly. Specific binder may non-covalently bind to the linked fluorescent molecules to form an assembly of composite which enhances fluorescent emission signals and improves energy transfer from donor to acceptor fluorophore, even under circumstances, whereby the absorption spectra of acceptor and emission spectra of donor are largely non-overlapping.

According to a second aspect, this invention provides the composition according to the first aspect of the invention in the form of a fluorescent probe.

In particular the probe may be used for coupling fluorescence emission to receptor-ligand binding. Preferably, the use of the probe provides coupling of fluorescence emission to receptor-ligand binding for providing simple homogeneous assays for a number of analytes whereby the signal enhancement or energy transfer is diminished by binding receptor to the probe.

The signal enhancement or energy transfer is preferably reduced by binding receptor to the probe molecule which prevents assembly with binder. The probe assembly construct serves as a convenient platform for fluorescence-based detection of various analytes because it may use a linker, which can be readily labeled with wide range of haptens or ligands.

Preferably, the use of the fluorophore probe is for assays where energy is transferred from at least one fluorophore to another.

The probe may be used for tagging materials, detection, diagnostics, high throughput screening, target validation, measuring of analytes and for measuring oxygen. The fluorescence compositions may be used for tagging purposes in life science and in counterfeit detection. The ability to detect target molecules such as proteins, antibodies, and nucleotides by tagging them with a fluorescent marker affords greater sensitivity for detection (Handbook of Fluorescent Probes and Research Products, Molecular Probes, Eugene, Oreg., Haughland, 2002). The probe may be used for tagging materials such a label.

When measuring analytes, the sample containing the analyte can originate from environmental sources such as waste water, drinking water, air, ground, soil or the sample can be a clinical sample obtained from serum, blood, faeces, urine, saliva, or milk. This invention can be applied to the detection and measurement of a broad variety of analytes including a drug, pharmaceutical compounds, metabolite, drugs of abuse, hormone, steroid, pesticide, environmental pollutant, food toxin, vitamin, protein, peptide, enzyme, hormones, polysaccharides, nucleic acid, DNA, RNA, antigenic marker, messengers, microbial surface marker, cancer cell marker, fungus, protozoan, virus, cell or tissue antigen. By way of examples only a few can be mentioned here:

aflatoxins
albumin
angiotensin
atropine
benzoyl ecgonine
biotin
cholinesterase
cocaine
c-reactive protein
cyclic AMP
digoxin
DNA
estrogen
folic acid
gentamicin
hemoglobin
High & low-density lipoprotein
immunoglobulin G
insulin
mycotoxins
myoglobin
parathyroid hormone
penicillin
phenobarbital
phenylpyruvic acid
polyaromatic hydrocarbons
porphyrin
prostate specific antigen
Protease
RNA
specific antibodies
theophylline
thiophosphate
troponin
vitamin B2.

Further examples of suitable analytes appear in patent U.S. Pat. No. 4,517,303.

Another group of analytes can be the environmental contaminants. For instance polyaromatic hydrocarbons (PAHs) are carcinogenic which can contaminate soil in many instances such as gas plant sites, coking operations, wood preserving with creosote, chemical and petrochemical plant waste disposal sites. PAHs are composed of two to six fused rings. The following are few examples of such pollutants: naphthalene, acenaphthalene, phenanthrene, anthracene, fluorene, acenaphthylene, benzo[a]anthracene, pyrene, fluoranthene, chrysene, benzo[b]fluoranthene, benzo[k]fluoranthene, benzo[a]pyrene, dibenzo[a,h]anthracene, indeno[1,2,3-cd]pyrene and benzo[g,h,i]perylene.

Analytes such as these can be detected in a more straightforward manner where only the analyte directly competes with at least one of the fluorophores, in the composition of the invention, for binding to the binder. Preferably the fluorophore that the analyte competes with is a also a polyaromatic hydrocarbon.

For instance the test probes 1 to 5, in example 1 have a pyrenyl moiety present which can compete with pyrene binding to binder in this way the intensity of fluorescence of FITC in the presence and absence of competing pyrene can be used to determine the level of pyrene. As free pyrene binds to the binder this lowers the binding of test probes 1 to 5 (example 1) to the same binder thus lowering signal of FITC when donor fluorophore (e.g. pyrenyl moiety of test probes 1 to 5) is excited at 345 nm. Other PAH can also compete similarly or probes. Test probes with other fluorescent PAHs can be constructed. Some examples of aromatic hydrocarbons that can be used to construct such test probes to monitor presence or absence of environmental pollutants include anthracene, acenaphthene, benzene, benzpyrene, benzanthracene, biphenyl, chrysene, coronene, dicyanoanthracene, phenanthrene, fluorene, fluoranthene, naphthalene, perylene, phenylanthracene, phenanthrene, pentacene, pyrene, stilbene, tetracene, triphenylene, toluene.

The invention may be used to monitor enzyme activity by introducing scissile bonds between the two fluorophores. In this way the probe composition is used as a fluorogenic substrate (Biophys. Chem. 67(1997), 167-176) for proteinases. The hydrolysis of peptide bond by enzyme then separates the two fluorophores so that the binder is no longer able to affect fluorescence changes as before. Test probe 1 having a lysyl residue treated with trypsin is no longer able to increase FITC signal when binding to binder such as rabbit serum albumin and when the excitation wavelength (345 nm) was suited to donor pyrene fluorophore.

The fluorescence intensity may be made to change by surrounding environment, including changes in temperature, light exposure, media, pH, solvents, and level of oxygen or simply by physical tempering.

The homogenous diagnostic aspect, according to this invention, may be achieved by design and synthesis of probes that (a) uses dye pairs, attached to a linker (such as peptide), which do not have any significant level of spectral overlap as normally required for FRET, (b) is responsive to efficient energy transfer in the presence of a binder which functions to enhance fluorescence emission whereby the emission band of the donor remains largely non-overlapping with absorption band of the acceptor, (c) after sensitisation with ligand or hapten and addition of receptor (R) gives changes in fluorescence emission which may be directly related to ligand or analyte concentration. The preferable means of detection is fluorescence spectroscopy, which includes but is not limited to commonly known methods based on intensity, lifetime, time correlation, photon counting, multiphoton, polarization, quenching, as well as FRET and photo induced electron transfer (PET).[1]

Preferably, the probe is used as a dye emitting light at wavelength bands or at intensities normally not achieved by ambient or visible light which may contain comparatively low intensities[2] of short wavelength light in particular in the ultraviolet band.

More than two fluorophores may be used for energy transfer, and analogues with more than two fluorophores and more than one linker may be used especially to transfer energy over longer wavelength ranges from one fluorophore to another arranged in series or parallel or randomly. These variations also fall under the scope of our patent.

A BRIEF DESCRIPTION OF THE DRAWINGS

The invention will now be described, by way of example only, with reference to the accompanying drawings FIGS. 1 to 16 in which.

Figure 7:
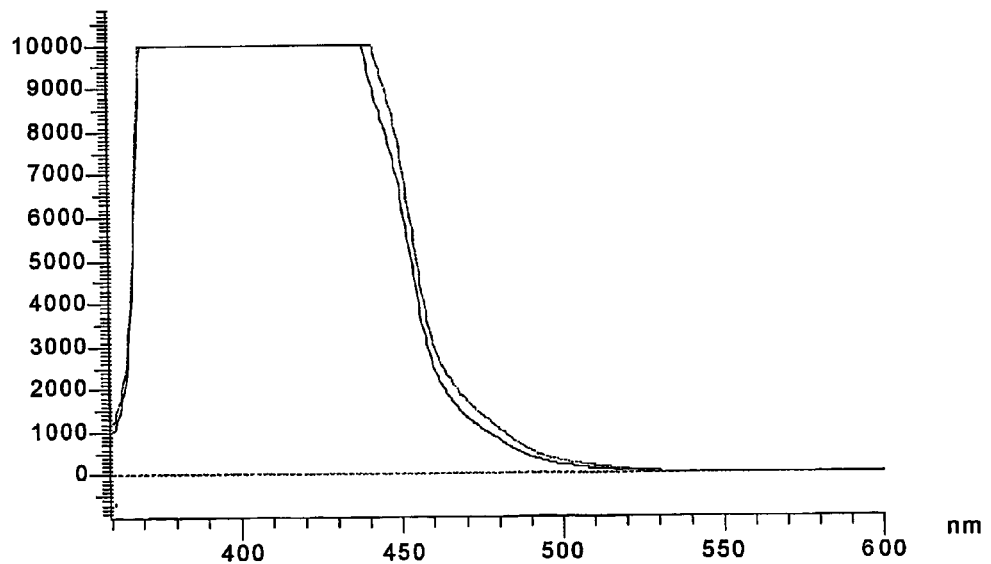
Figure 8:
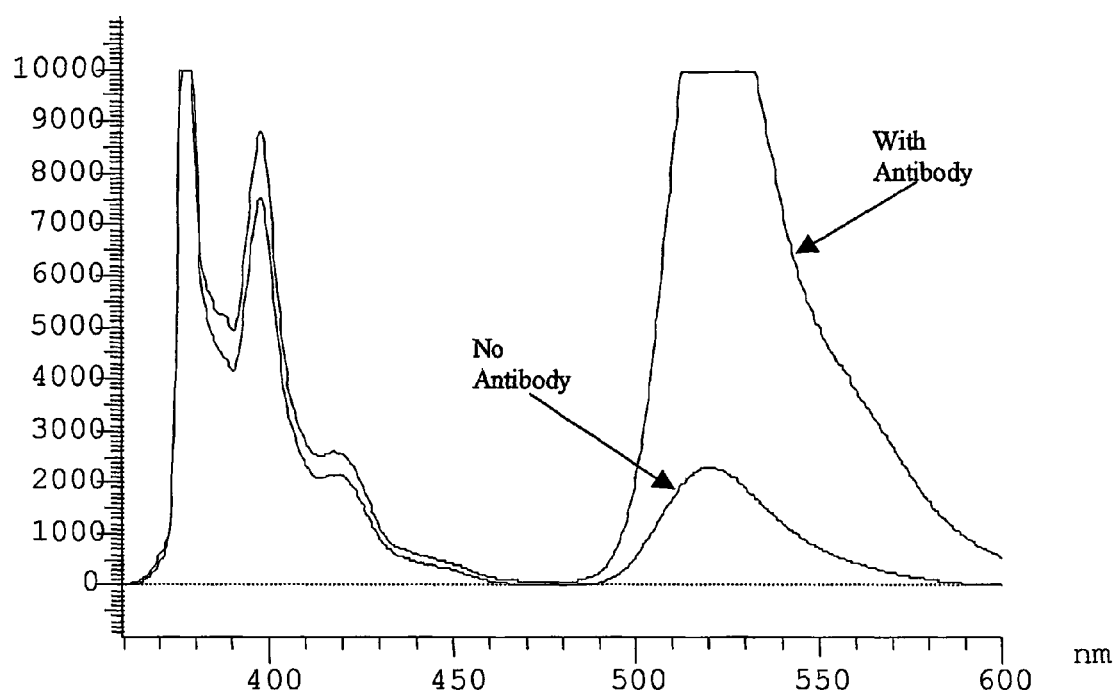
Figure 10:
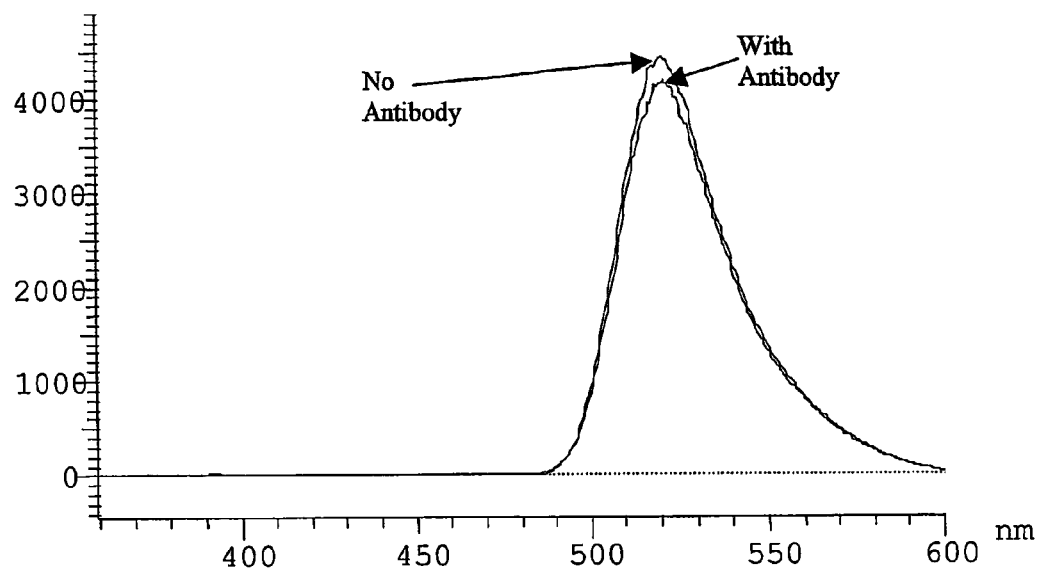
Figure 11:
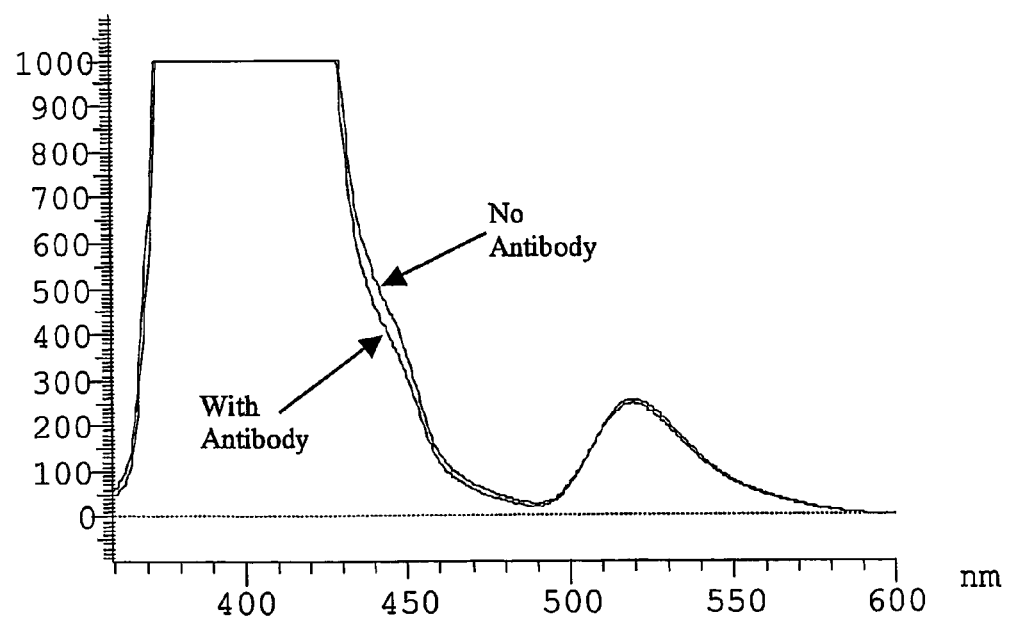
Figure 12:
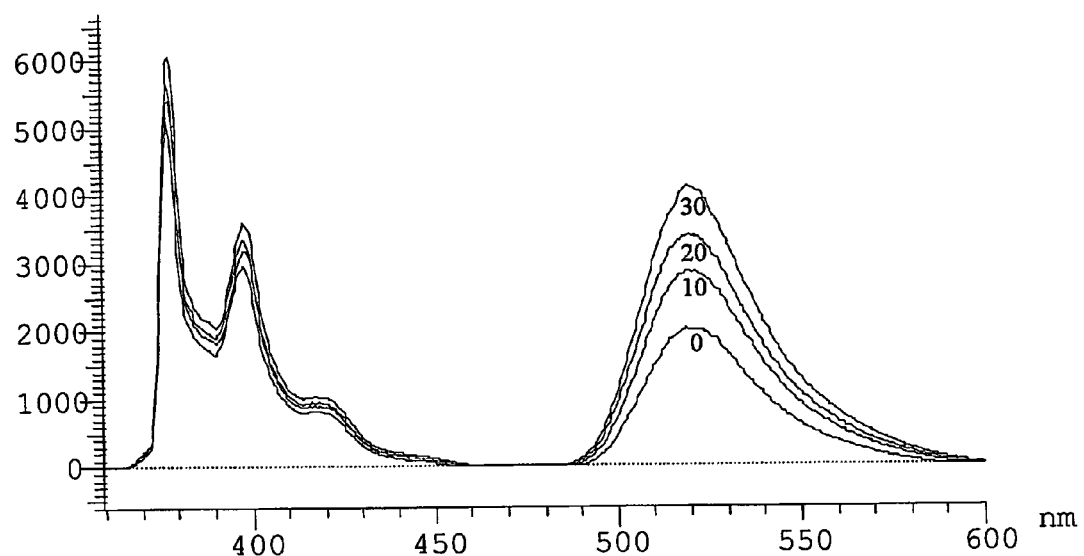
Figure 13:
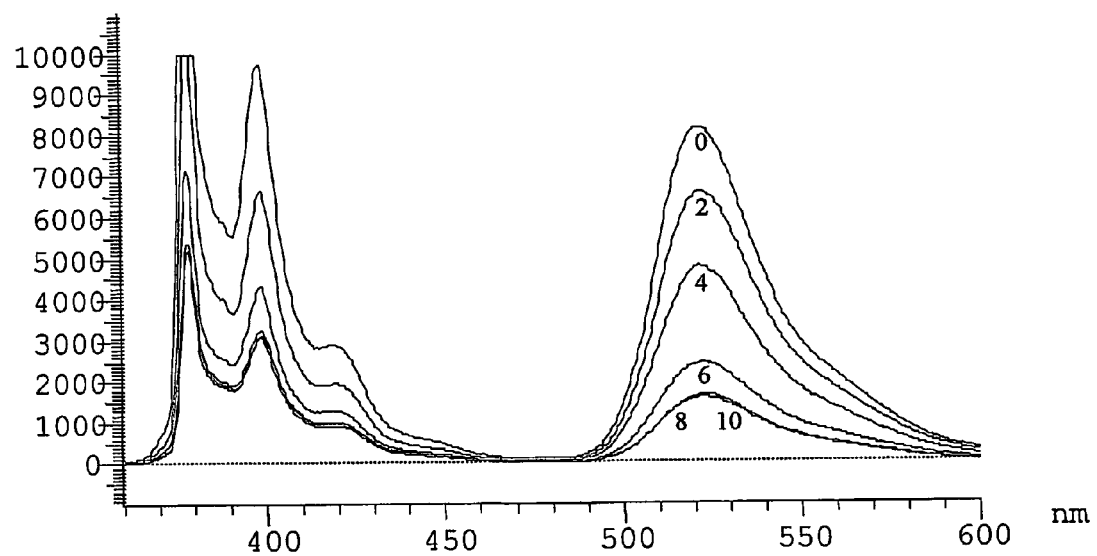
Figure 14:
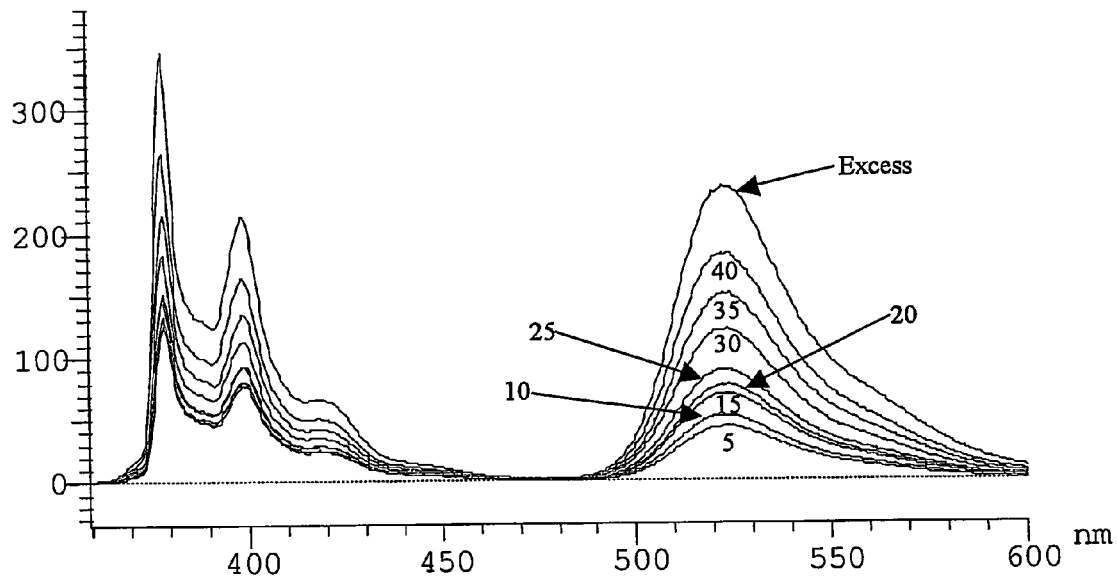
Figure 14:
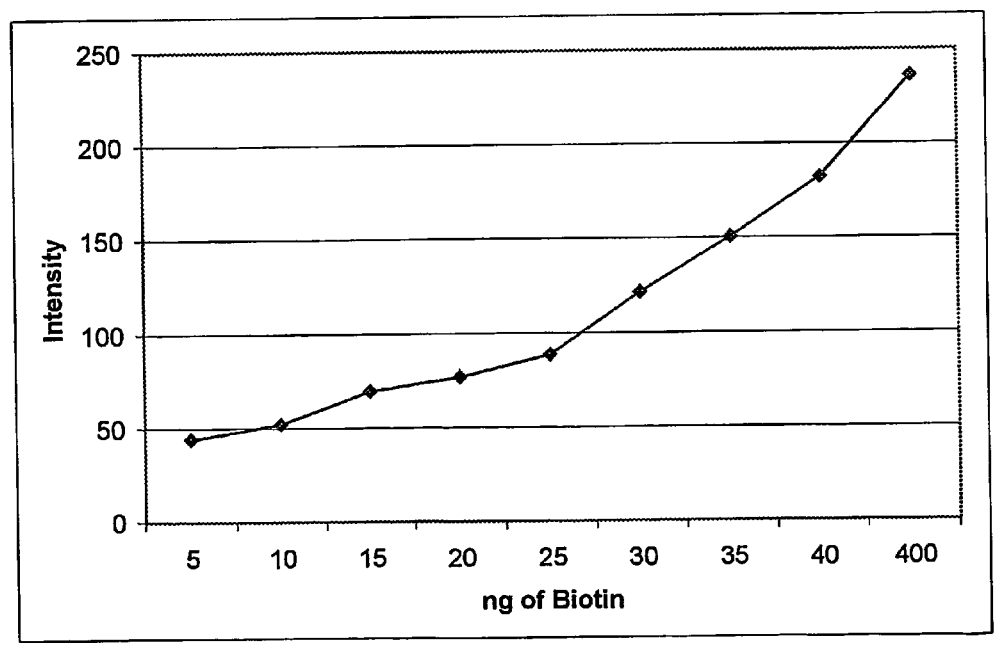
Figure 15:
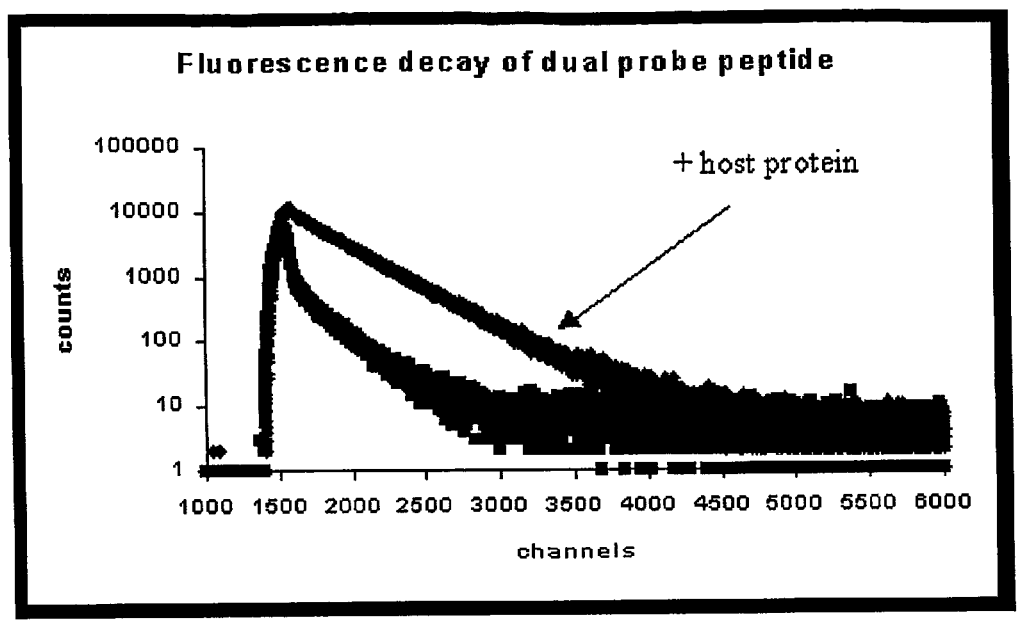
Figure 15:
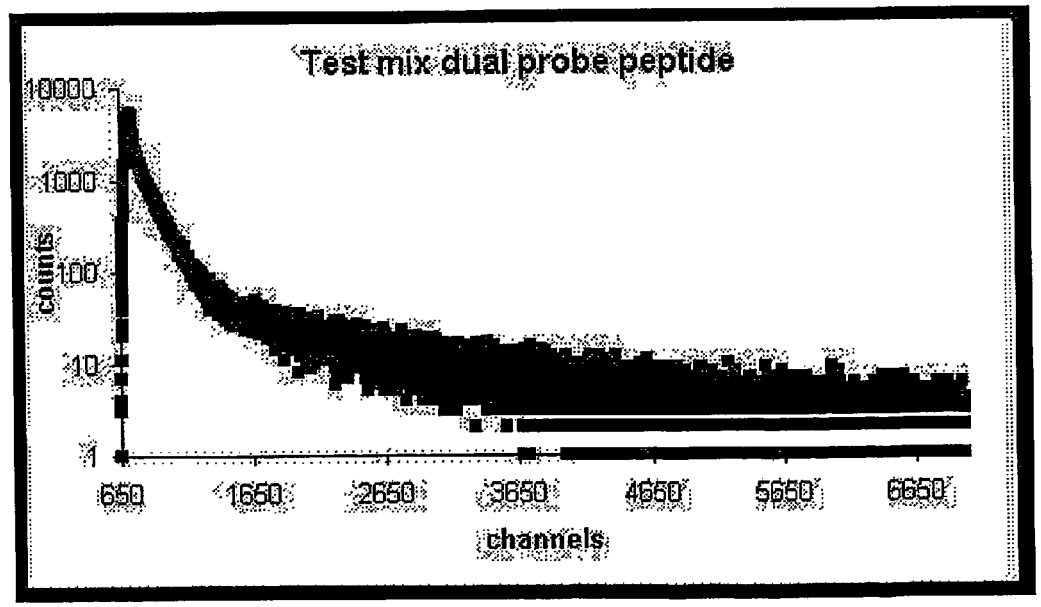
Figure 16:
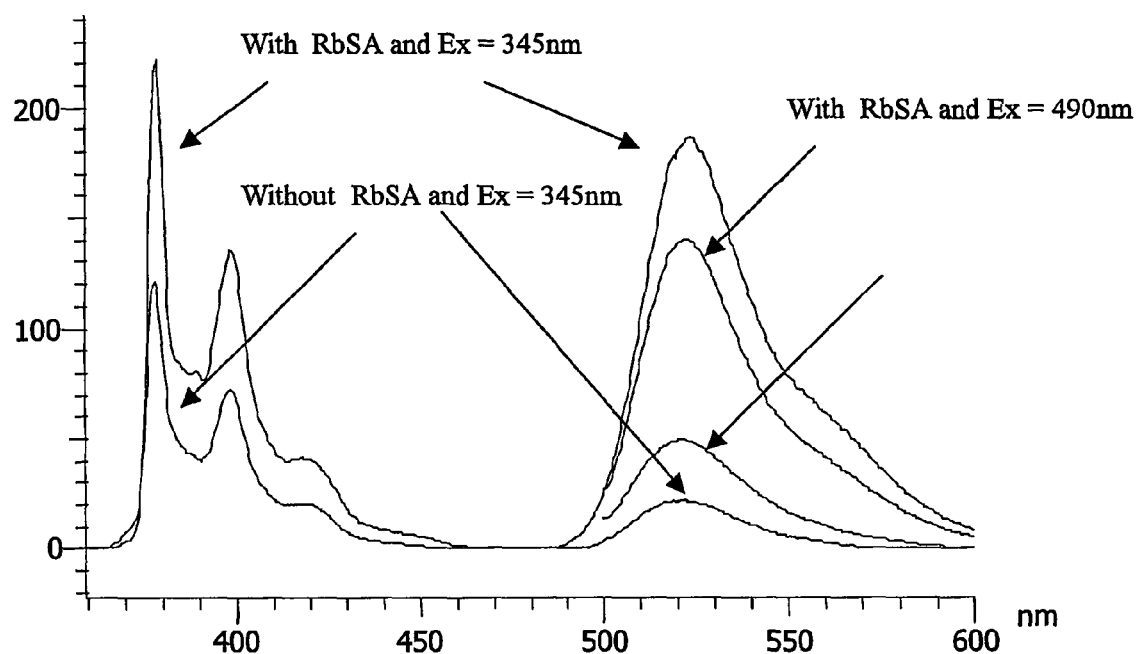

FIG. 7 is a graph illustrating the emission spectrum of control probe 2; in this experiment 20 µl of 1 mg/ml Control 2 was suspended in 2 ml PBS buffer and then 80 µl of fresh antipyrene (1:10 dilution) added the spectra are almost indistinguishable in appearance, excitation wavelength was 345 nm;

FIG. 8 is a graph illustrating the results of test probe 1 in the presence and absence of 80 µl antipyrene antiserum (1:10 diluted) excited at 345 nm;

FIG. 9a is a graph illustrating the results of the emission spectrum of FITC with RSA titrated to different levels;

FIG. 9b is a graph illustrating the results of various binders test probe, in this experiment 2 ml of PBS with 20 µg Test probe1 and 30 µl of binder (7 mg/ml), was excited at 345 nm;

FIG. 10 is an emission spectrum of control probe 1 in the presence and absence of antipyrene antiserum when excited at 345 nm;

FIG. 11 is a graph illustrating the results of a mixture of control probe 1 and control probe 2; excitation wavelength was 345 nm;

FIG. 12 shows the results of the screening of avidin protein with test probe 1;

FIG. 13 is a graph showing the results of the addition of various levels of streptavidin to test probe 2 in the presence of RSA; excitation wavelength was 345 nm;

FIGS. 14a and b shows the results of biotin pre-incubated with streptavidin and test probe 2 with RSA; excitation wavelength was 345 nm;

FIG. 15a are graphs showing fluorescent decay profiles when probe 2 was excited at emission wavelength to suit pyrene excitation in the presence and absence of RSA as host protein and fluorescence decay measured, further treatment of this mixture with streptavidin provided test mix of probe 2 (having pyrene and FITC as dual fluorophores) plus RSA+ streptavidin giving decay profile as in FIG. 15b;

FIG. 16 is a graph showing the results of a full emission spectrum of test probe 2 in the presence and absence of RSA excited at 345 and 490 nm.

EXEMPLIFICATIONS

The following examples illustrate specific applications of the invention. These specific examples are not intended to limit the scope of the invention described in this application.

Example 1

Figure 1:
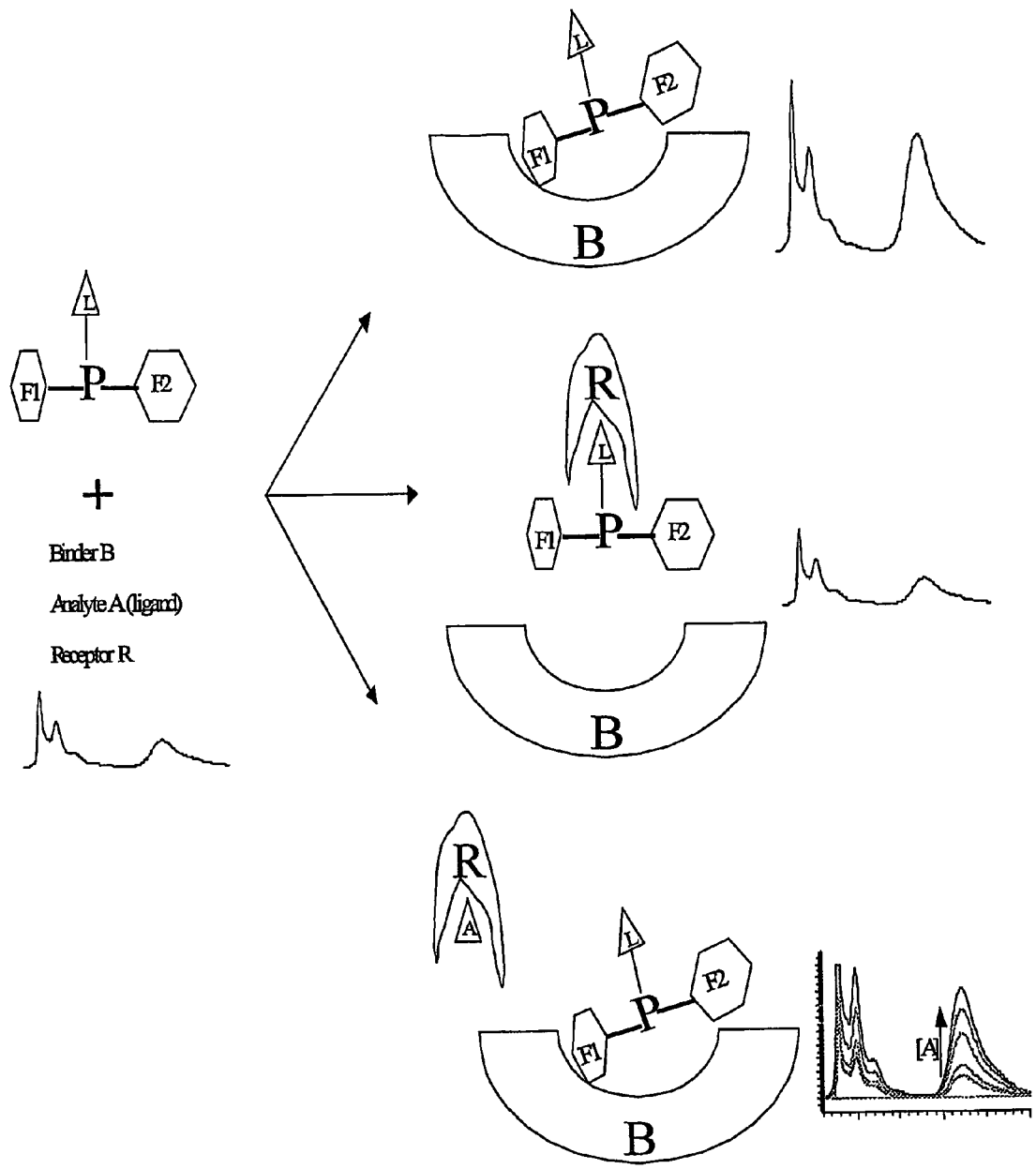
FIG. 1a is a schematic illustration of a homogenous diagnostic aspect in accordance with the invention.
FIG. 1b is the chemical structure of test probe 2.
Figure 1:
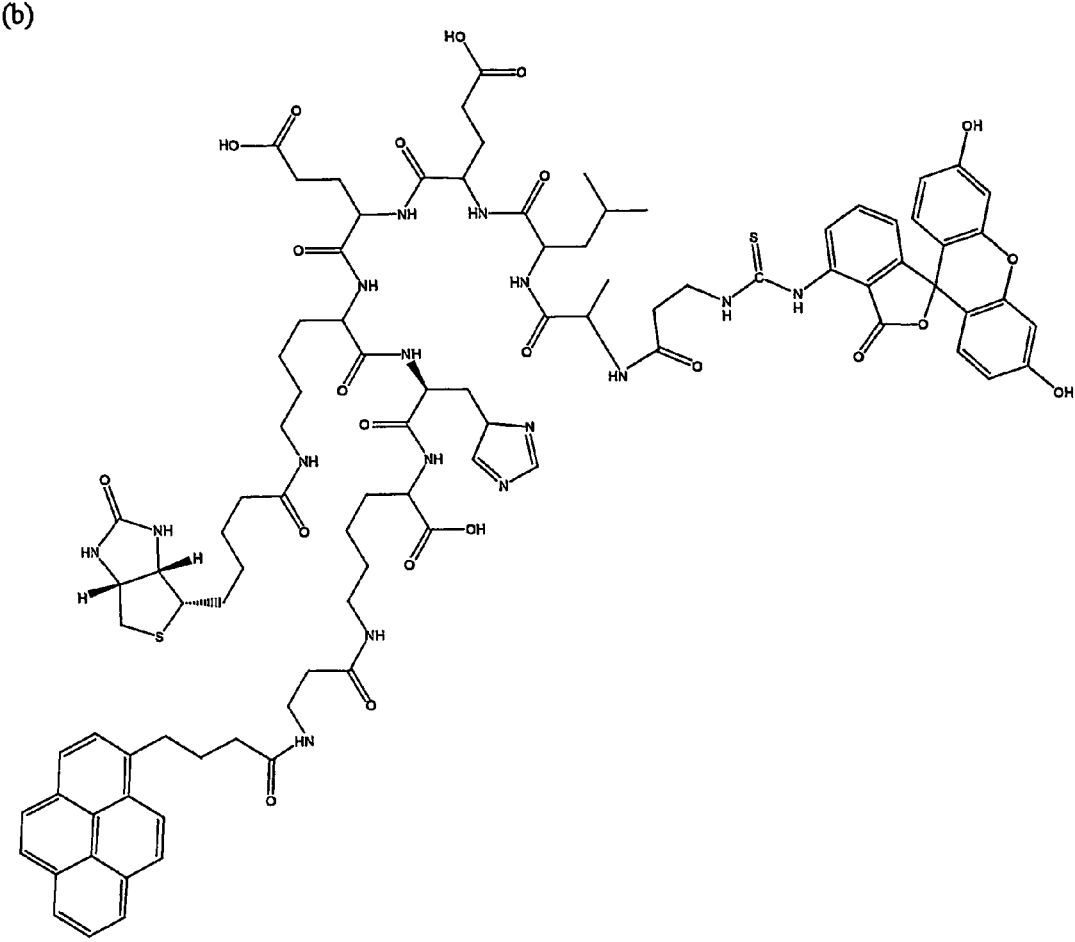

A schematic of a homogeneous diagnostic aspect of the invention is shown below in FIG. 1 in which A is analyte, B is binder, F1 and F2 are fluorophores, L is ligand or hapten, P is linker and R is receptor. The fluorophores, F1 and F2, have the structure F1-P-F2, where P is a linker, that maintains F1 and F2 in a configuration which need not be compatible with FRET (particularly when not bound to binder B) and may have a site for conjugation to ligand (L) or analyte (A). F1 is a fluorescent donor capable of causing an acceptor moiety to fluoresce by energy transfer efficiently in the presence of specific binder (B) and F2 is a fluorescent acceptor capable of accepting energy when F1 is excited. These compounds are useful as fluorescent probes for diagnostics and labels.

This example selects pyrene (Pyr) and fluorescein (FITC) as fluorophore dye pairs which are atypical for performing FRET. This is particularly the case when pyrene is present as monomer. In our examples at least one and typically more linked dye pairs are constructed into the composition, such that fluorescein fluoresces efficiently at the excitation of wavelength of pyrene monomer in the presence of binder.

When a biotin ligand or hapten is also coupled to the linked pyrene-fluorescein in the presence of the rabbit serum protein as binder, an assay for biotin is achieved as a result of the biotin-binding streptavidin preventing or disrupting the formation of the fluorescent assembly. Thus in the presence of free biotin, less streptavidin is able to bind to the linked fluorophores, more of which are available to form assemblies, and so higher fluorescence results. In this way the signal increases with an increase in analyte concentration can be obtained which is considered advantageous, as it is not always possible to attain this in a normal homogenous competitive assay.

Example 2

Probes and their Fluorescence Spectroscopic Properties

Fluorescence measurements were made on a Hitachi F-2500 fluorescence spectrophotometer with a 1 cm path length cuvette. Spectra were measured at a rate of 1500 nm/min. Excitation wavelength of 345 nm was used for pyrene and 490 nm for FITC.

The machine sensitivity was set at 700 v or 400 v depending on the concentration and fluorescence intensity of the sample. Absorption spectra were recorded on Hitachi U2010 spectrophotometer. Lifetimes were measured on modified IBH machine.

Given below are structures of linkers (here peptide is used as linker) and F1-P-F2 and conjugates F1-P (L)-F2. Three-letter code is used for amino acids. F1 is fluorophore 1 for instance pyrenebutanoyl pyr), F2 is fluorophore 2 for instance fluorescein isothiocynate (FITC). L is ligand or hapten for instance biotin. L can be linked to any part of the F1-P-F2 including the F1 and F2. For Lys(βAla), the carboxyl of βAla is linked to epsilon amino of lysine via an amide bond.

FITC is conjugated to amino of β Ala

Linker: βAla-Ala-Leu-Glu-Gln-Lys-His-Lys(βAla)-amide

Test Probes:

1:

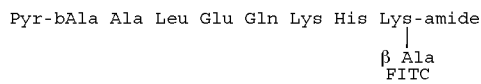

2:

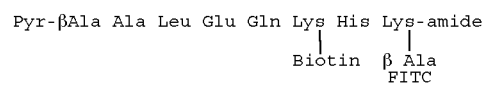

3:

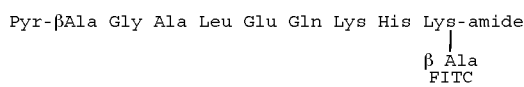

-continued

4:

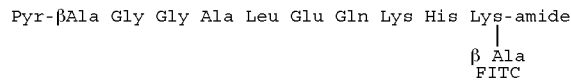

5:

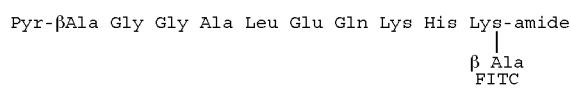

Control Probes:

1:

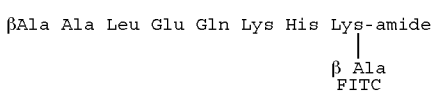

2:

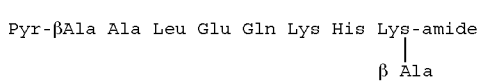

The chemical structure of test probe 2 is shown in FIG. 1b.

The compounds above can be made by solid-phase and solution phase synthesis methods. For instance the linker peptide sequence can be readily prepared by t-Boc solid-phase synthesis using 0.5 mmoles of p-methylbenzhydrylamine (MBHA) resin which provides an amide C-terminal group upon cleavage. The Boc amino acid (BACHEM, UK) side chain protections used were benzyl for Glutamic acid; Tosyl for histidine; fluorenylmethyloxycarbonyl for C terminal Lysine and 2-chloro-benzyloxycarbonyl for the second lysine. The Boc group was deprotected by treatment with 50% trifluoroacetic acid in dichloromethane (DCM). After several five washes with DCM neutralisation was carried out with 5% solution of DIPEA (diisopropylethylamine) in DCM. Couplings were made using 1.5 mmoles of amino acid, 1.5 mmoles of BOP (Castro's reagent) and 4.5 mmoles of DIPEA in DMF for 40 minutes. Second coupling was used, when necessary, to drive the reaction to almost completion (>99.8%). The first lysine incorporated (N-α-t-Boc-N-ε-Fmoc-L-lysine) had fmoc protection on the epsilon amino. This was selectively removed by treatment with 20% piperidine in DMF for 20 mins followed by washes with DMF. Fmoc-βAla-OH was then coupled on the side chain as per standard coupling. The rest of the sequence was assembled in the usual linear fashion using Boc chemistry. Pyrene butyric acid was coupled in the same manner as an amino acid. At the end of peptide assembly the peptide was treated with 20% piperidine in DMF for 20 mins followed by five washes with DMF and FITC was coupled by an overnight reaction using 1.5 equivalent of FITC in pyridine/DMF/DCM (12:7:5). The resin was then washed with DMF and DCM and finally dried. The products were cleaved from the resin using HF in protection in the presence of 0.5 g p-thiocresol and 0.75 g p-cresol as scavengers. After removal of HF the peptide were precipitated with anhydrous ether. To label the peptide with biotin in solution phase the peptide (0.02 mmoles) was dissolved in 2 ml of DMF and biotin N-hydroxysuccinimide (0.1 mmoles) was added followed by DIPEA (0.3 mmoles). The peptides were purified on a C-4 reverse phase semi-preparative column (Vydac C-4, 250×4.6 mm) using an acetonitrile/0.1% TFA gradient. Elution was monitored by absorbance at 220 nm and flow rates were 8 mL/min. The purity of the peptides was determined by analytical reverse phase HPLC at 1 ml/min flow rate. The structure was confirmed by laser desorption mass spectrometry using Lasermat 2000 thermobioanalysis mass spectrometer.

Firstly we consider the F1 and F2 individually without linker to select a suitable atypical FRET pair. F1 is represented by pyrene butyric acid and F2 by FITC. Rabbit serum albumin was used as binder. These chemicals were purchased from Sigma-Aldrich Chemical Co.

Figure 2:
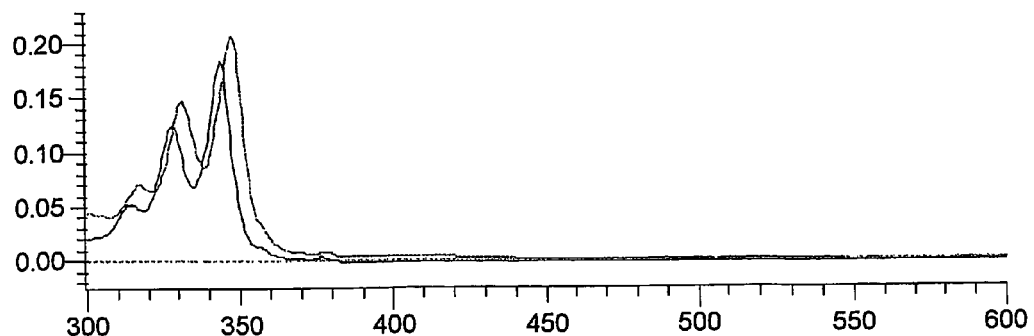
FIG. 2a is a graph illustrating the absorption spectra of 6 µM pyrene butyric acid in a PBS buffer; with and without RSA, the spectrum with a very slightly higher intensity is with RSA.
FIG. 2b is a graph illustrating the absorption spectra of 6 µm FITC in PBS; with and without RSA; the spectrum with a very slightly higher intensity is with RSA.
Figure 2:
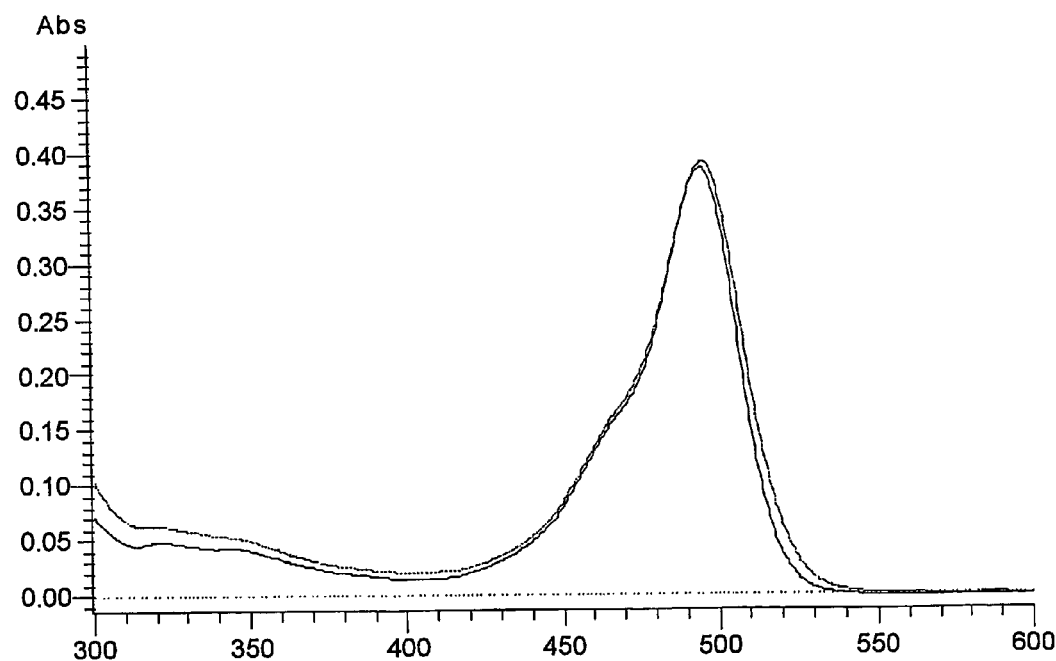

FIG. 2a shows the absorption spectra of pyrene butyric acid in PBS buffer. It is clear that pyrene absorbs strongly at 345 nm and this can be selected as the most efficient wavelength. Addition of rabbit serum albumin (RSA) shows a slight effect (3.5 nm shift) on the $\lambda_{max}$ of absorption although the absorption value remained almost constant at 345 nm in this solution. FIG. 2b shows the absorption spectra of FITC in PBS. The absorption spectrum of FITC appears to not to change with addition of RSA as a binder as the two spectra are almost indistinguishable. The $\lambda_{max}$ of absorption for FITC is around 490 nm although there is relatively weak absorption at 345 nm.

Figure 3:
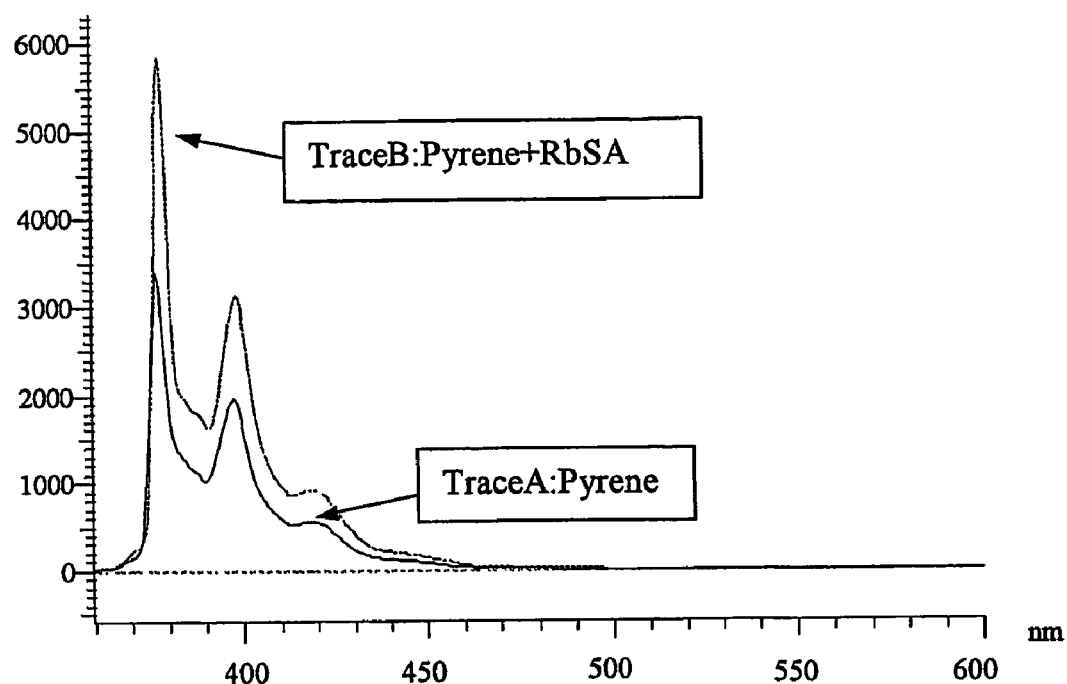
FIG. 3 is a graph illustrating the emission spectrum of 0.3 µM pyrene butyric acid when excited at 345 nanometers, with and without RSA (1.5 mg)
Figure 4:
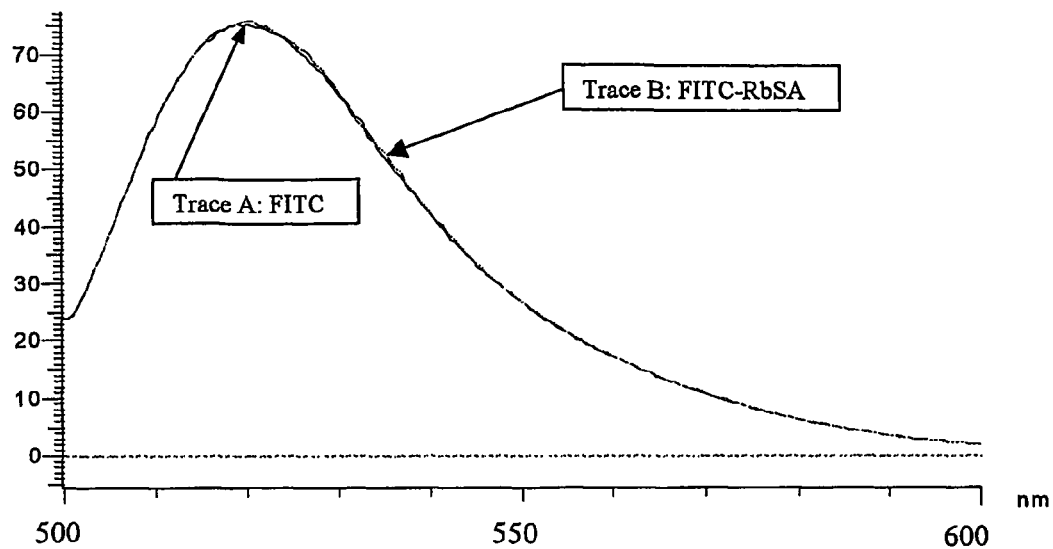
FIG. 4a is a graph illustrating the emission spectrum of 0.3 µM FITC when excited at 490 nanometers, with and without RSA (1.5 mg)
FIG. 4b is a graph comparing the intensity of a solution of 0.3 µM FITC when it is excited at 490 nanometers (trace A) and 345 nanometers trace B.
Figure 4:
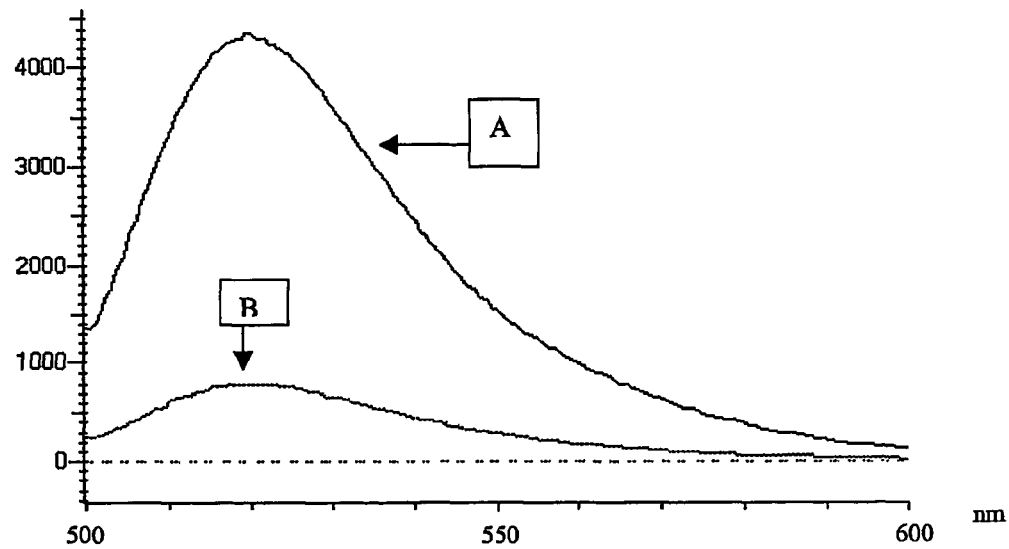
Figure 5:
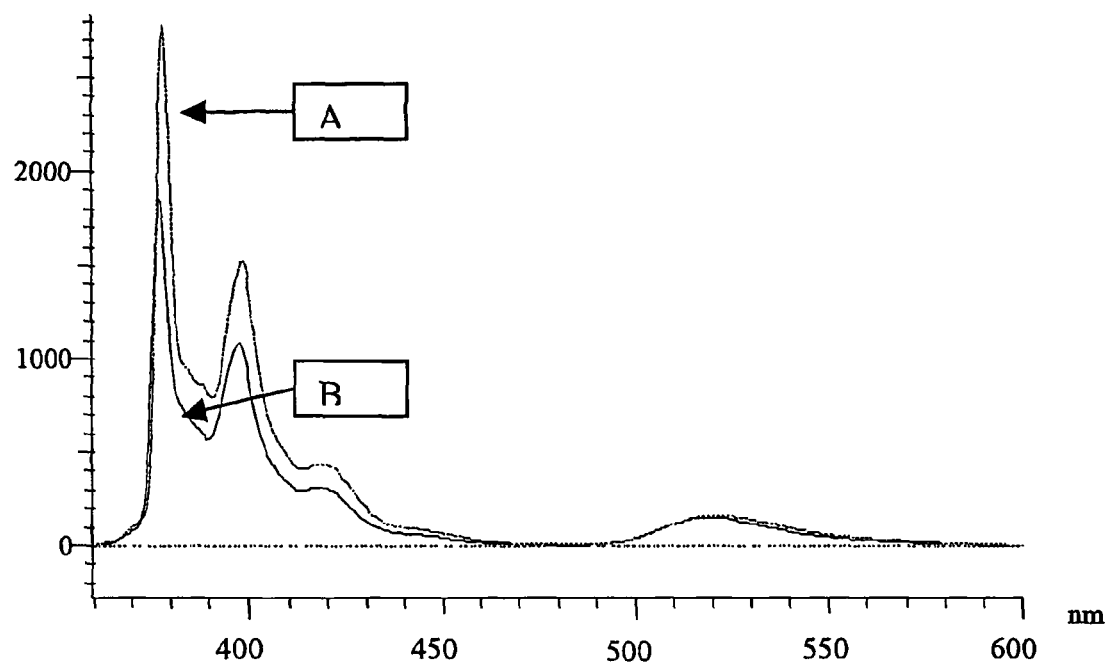
FIG. 5 is a graph illustrating the emission spectre of a 1:1 equimolar mixture of pyrene butyric acid and FITC in the presence (trace A) and absence (trace B) of RSA, excited at 345 nm.

The emission spectrum of pyrene when excited at 345 nm is shown in FIG. 3 trace a. A typical monomer spectrum is evident with emissions peaks at around 377 and 397 and a small shoulder at 418 nm. The addition of the binder (RSA) has the effect of increasing the fluorescence intensity without any obvious shift in wavelength maxima as shown in trace b. Note that the emission is unaffected at wavelengths above 450 nm where FITC is expected to absorb strongly (FIG. 2b). A solution of FITC prepared in PBS pH 7.4 when excited at its $\lambda_{max}$ absorption (490 nm) gives an emission maxima around 520 nm both in the presence or absence of RSA (FIG. 4a). Like its absorption spectrum, the emission spectrum of FITC also appears not to change with the addition of the binder. A similar observation was made if FITC solution is excited at 345 nm except that the overall intensity observed by exciting at 345 nm is relatively small. FIG. 4b compares the intensity of a solution of another FITC when its is excited at 490 nm (trace a) and 345 nm (trace b) with the latter wavelength showing a significantly high signal. Overall, comparison of the data thus reveals that the emission of pyrene (370-430 max 377 nm) does not, to any appreciable level, overlap with the absorption ($\lambda_{max}$ 490 nm) of FITC and this is one of the key conditions of our invention. In this respect, little or no FRET can be expected from this pair of fluorophores and we classify these as atypical fret pair. To clarify this further, and rule out possibility of dye to dye interaction, FIG. 5 shows the emission spectra of 1:1 mixture of pyrene butyric acid and FITC in the presence and absence of RSA. While the pyrene fluorescence (trace A) is enhanced the fluorescence of FITC (trace B) is hardly affected. The small amount of fluorescence observed at 520 nm (trace B) is merely due to small direct excitation of FITC by 345 nm wavelength which can be expected as FITC has a relatively small absorption at 345 nm compared to 490 nm (FIG. 2b). It can be concluded that the fluorophores in this mixture are acting independently and also that the lack of any appreciable spectral overlap makes them unsuitable for normal FRET. It is also apparent that the free fluorophores in the mixture show little or no enhancement of FITC (F2) signal with the binder and there is no evidence of excimer or exciplex complex formation as indicated by almost indistinguishable spectra beyond (>420 nm) the pyrene monomer signals.

Figure 6:
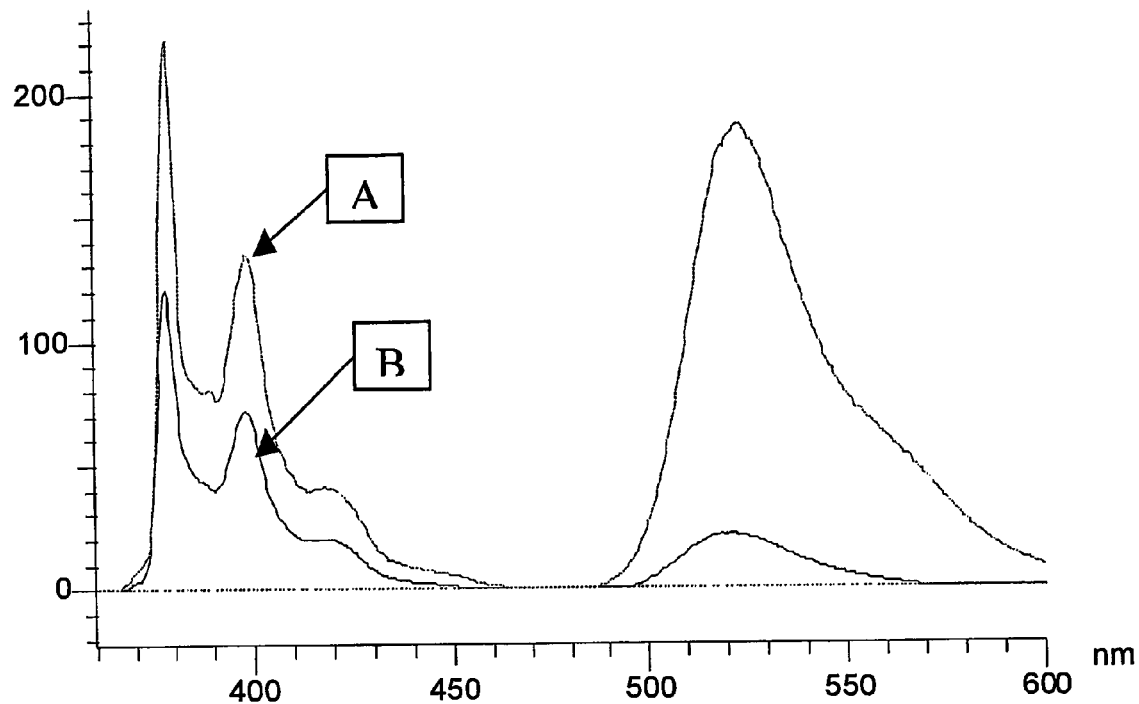
FIG. 6 is a graph illustrating the spectrum of 0.5 ml solution containing 5 µg test probe 1, with and without RSA (0.375 mg)

The spectrum (FIG. 6) of test probe 1 comprising both these fluorophores when linked with flexible peptide also corroborates this finding with only a low level of FITC fluorescence present when F1, pyrene, is excited (345 nm) in the absence (trace B) of the binder. Again low level fluorescence most likely arising from slight but direct excitation of FITC at 345 nm where this fluorophore absorbs very weakly (FIGS. 2b and 4b). Clearly the emission of F1 remains substantially outside the absorbing range of F2 and yet significant fluorescence enhancement of F2 is observed in the presence (FIG. 6 trace A) of the binder when the fluorophores are linked. Thus, the linked FITC and pyrene as fluorophores F1 and F2 continues to act as an atypical FRET pair and when a contact with a binder is made a substantial rise in fluorescence enhancement of FITC is observed. In addition, it is noteworthy that no excimer (max 470 nm) or exciplex is formed from pyrene as its spectrum (FIG. 6) remains typical of a monomer with emissions at 377 and 397 and 418 nm, as found for free pyrene, irrespective of binder protein. This is further confirmed (FIG. 7) by the emission spectrum of control probe 2, without having F2 (FITC), also showing the presence of monomer and absence of excimer or exciplex signal irrespective of binder (RSA) protein.

In the preferred embodiment at least one of the fluorophore is a polyaromatic hydrocarbon or a hetrocyclic. F1 and F2 can be any fluorophores as long as little or no fluorescence from F2 is present when F1 is excited in the absence of a binder. Some examples include, but are not limited to a fluorophore selected from the group consisting of pyrene, perylene, coronene, porphyrin, naphthalene, acridine orange, Edans, Eosin, Erythrosin, Oregon Green, cyanines, fluorescein, FAM, rhodamine, TET, JOE, HEX, TAMRA, phycoerythrin, phycocyanin, anthracene ring allophycocyanin, o-phthaldehyde label, fluorescamine, tetramethylrhodamine and BODIPY, ROX, Texas red.

Example 3

Screening for Suitable Binders B

A binder is any compound that interacts with the composition so that fluorescence emission of acceptor is enhanced when the donor is excited. This includes solvents of different dielectric constant. The binder's function could be to merely interact with compositions to enhance their fluorescence. Also the binder function may be to provide local environment of different dielectric constant to shield the compositions from bulk solution. For instance binder can be a protein capable of binding to any part of the F1-P-F2 or its conjugate with other molecules. The binder can be specifically prepared for instance by raising antibody against part of the molecules such as one of the fluorescent dye or its analogues conjugated to carrier protein. Latter analogues may include more than one composition linked together or compositions conjugated to other compounds or particles. Antibodies could be produced by standard practice of conjugating molecules for instance pyrene with a carrier protein either with or without linker. Such procedures of bioconjugation and producing antibodies are commonly known (Antibodies: A Laboratory Manual (1988) by Ed Harlow, David Lane Cold Spring Harbour Laboratory). For instance, antipyrene antiserum raised against a hapten pyrenyl-Lysyl-glycyl-lysyl(pyrenyl)-Cys-Lys-Asp-Asp-amide conjugated to BSA or KLH were prepared and shown to enhance fluorescence of fluorescein when pyrene of test probe 1 was excited at 345 nm. This is illustrated in a typical spectrum shown in FIG. 9a in the absence and presence of binder which was antiserum (anti-pyrene added in the form of diluted 1:10 antiserum diluted with PBS pH 7.4). The binder enhances the fluorescence emission of F2 (FITC) when excited at 345 nm.

Alternatively, the binder may be found by standard screening methods including solution phase ligand binding assays or solid phase binding assays. Proteins with hydrophobic pockets could be used as binders. In addition, one may be able to modify the molecule to create a hydrophobic pocket for docking a composition into. For instance haem group from myoglobin can be removed to prepare apoprotein, which could be used as suitable binder (Biochem. J. (1986) 237 (613-616)). The binder is not restricted to proteins. For instance cyclodextrins, crown ethers, liposomes, polymers and particulates can also be used as binders. To evaluate if a compound is suitable as a binder the solution of test probe 1 was prepared and its fluorescence emission at 520 nm recorded by excitation at 345 nm. Any compound that changes the F2 signal when F1 is excited could be used as binder. Preferably, the binder increases the signal. Screening other serum proteins reveals that rabbit serum alone can be used as a binder in the case of this particular assembly. This is shown in FIG. 9b a where the test probe 1 is titrated with aliquots of rabbit serum albumin and emission intensity increase is observed in response to added binder. In this example, 2 ml of 5 µM Test Probe 1 in PBS is treated with 0, 10, 20, 30 µl additions (indicated on the spectra) of 7 mg/ml of rabbit serum albumin (RSA) purchased from sigma. The excitation wavelength was 345 nm. Emission spectra representing the fluorescence intensity against the wavelength are displayed. The fluorescence of F2 (FITC) increases more significantly than F1 (pyrene) as RSA is added. Clearly, the acceptor (FITC) fluorescence (520 nm) is significantly (>2fold) enhanced in the presence of the binder. Using similar experiments we found that rabbit serum albumin (RSA), human serum albumin (HSA), Beta cyclodextrins, avidinand apoprotein, could enhance the signal to a varying extent (FIG. 8). Another way of assessing if a compound is suitable as a binder would be to evaluate the change in fluorescence intensity of the F1 signal when the binder is added. In this regard, the pyrene emission signal increases when RSA was added in the examples provided (FIG. 8). Media with different dielectric constants will tend to increase this signal to varying levels (J. Fluoresence vol. 10(2000) No. 1 pages 1-6). Any fluorophore could be studied in the same way to asses it as a potential F1 candidate. Many compounds including albumins and spectrin are known for their ability to bind fluorophores and enhance the fluorescence intensity (J. Pharmacobio-Dyn, 12 (1989) 762-770) and could be used.

Example 4

Spectroscopic Properties and Signal Enhancement with Binder

Figure 9:
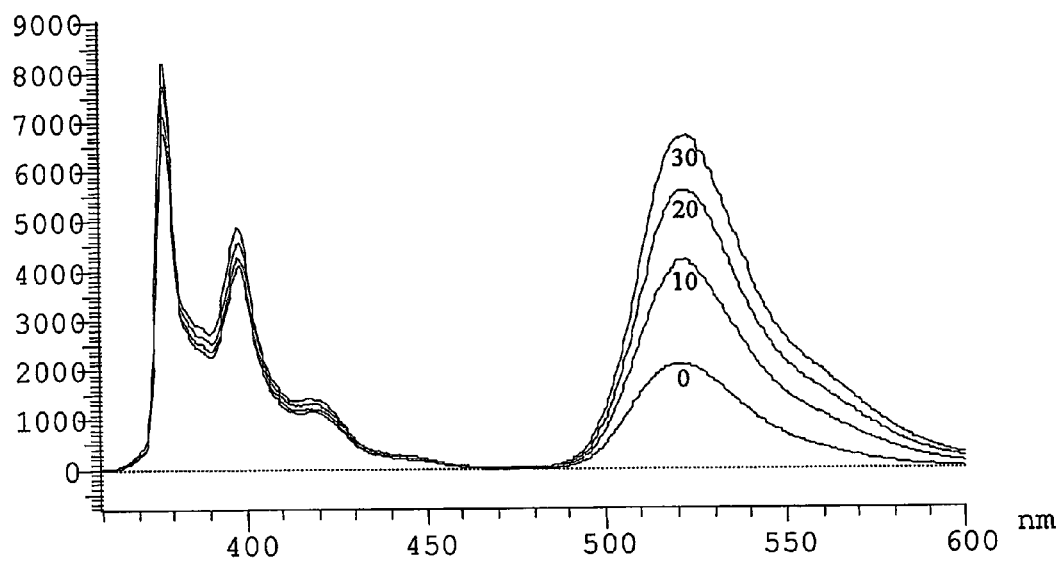
Figure 9:
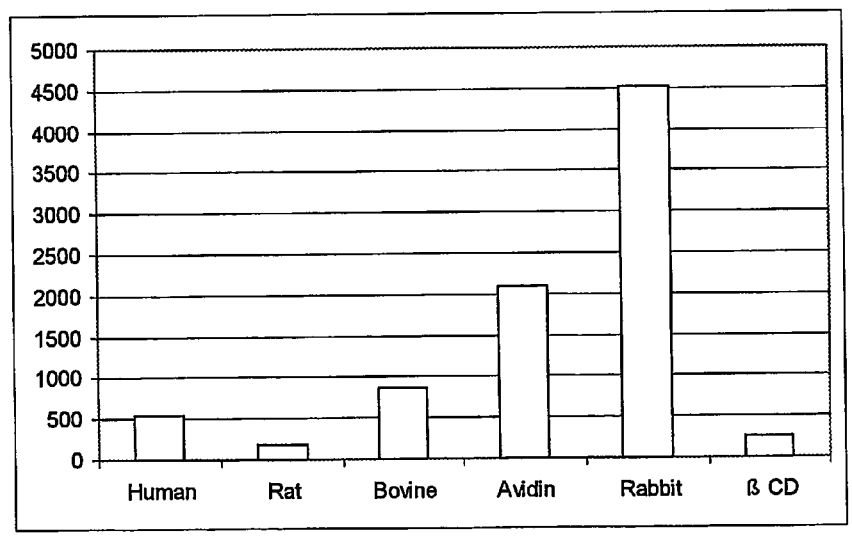

Test Probe 1 shows an intense increase in the FITC signal ($\lambda_{max}$ emission around 520 nm) when antipyrene antiserum antibody is present (FIG. 9). The excitation wavelength was 345 nm. Emission spectra representing fluorescence intensity against wavelength are displayed in FIG. 9 for 2 ml of 5 µM test probe1 in PBS (phosphate buffered saline pH 7.4) treated with 80 µl of anti-pyrene antibody (1:10 dilution of antiserum). Similar experiments to above but with control probe 1 lacking F1 (no pyrene attached) showed no appreciable change in emission of FITC in the presence of binder indicating F1 is required for efficient energy transfer. This is shown in FIG. 10. In this example a 2 ml of 6 µM control probe 1 in PBS is treated with 80 µl of anti-pyrene antibody (1:10 dilution of antiserum). Excitation wavelength was 345 nm. Emission spectrum representing fluorescence intensity against wavelength is displayed. The fluorescence intensity observed is merely due to direct excitation of FITC since, as explained above, (FIG. 6) the FITC does have slight absorption in this region. In another experiment we observe that control probe 2 (without FITC) showed little or no emission above 500 nm indicating that the observed fluorescence above 500 nm in FIG. 10 was due to FITC. In fact, all test probes of example 1 have been screened against RSA and like test probes 1 and 2 the test probes 3, 4 and 5 also showed significant enhancement of FITC when the binder was present to varying levels.

Taken together these experiments reveal that fluorescence intensity (520 nm) of F2 is significantly enhanced by assembly with the binder.

Example 5

Role of Linker 1 ml of 5 µM Control probe 1 and 1 ml of 5 µM Control probe 2 were simply mixed and showed (FIG. 11) negligible change of FITC (F2) signal (fluorescence above 500 nm) when 80 µl of anti-pyrene antibody (1:10 dilution of antiserum) is added. Excitation wavelength was 345 nm. This example highlights the role of the linker to form the covalent linkage between the fluorophores. This also agrees with the above findings when free fluorophores were used in example 1. The linker is preferably flexible, water-soluble and has a site that can either bind to the receptor or is capable of being modified by a hapten or ligand. Any cross-linkers whether they are homofunctional or heterofunctional can also be used. Linkers may include, but are not limited to, alkyl spacers, polyethylene oxides, polyamino acids, polyamides, fatty acid chains, and DNA. The only requirements is that the F1 and F2 are inked in such a way that low fluorescence is present when F1 is excited in the absence of binder but higher when a binder is present.

Example 6

Screening avidin and streptavidin proteins with Test Probe 1 reveals that the avidin (FIG. 12) can be used as a binder but the latter had very little effect on FITC signal. In this example, 2 ml of 5 µM Test Probe 1 in PBS is treated with 0, 10, 20 and 30 µl of avidin solution as indicated on the spectra. Excitation wavelength was 345 nm. Emission spectra representing fluorescence intensity against wavelength are shown for avidin.

Example 7

Measuring Analyte (Biotin)

A signal was generated by adding RSA (rabbit serum albumin) to Test Probe 2 in the presence of streptavidin (receptor R) aliquots which were 0, 2, 4, 6, 8, 10 µL additions as marked on the spectra. The decline in signal with the increase in the level of receptor is evident (FIG. 13). In this example, 0.5 ml solution of 5 µM Test probe 2 in PBS buffer and 52 µg of RSA were used. The excitation wavelength was 345 nm. The signal declines in response to specific binding by streptavidin. This could be used to form the basis of an assay for biotin.

In the analyte (A) test experiment, biotin pre-incubated with streptavidin (receptor R) was added to Test Probe 2 and rabbit serum albumin used as the binder (B). Biotin concentration-dependent signal was obtained which was directly proportional to the analyte (biotin) concentration. FIG. 14a shows the increase in the emission with increasing amount of biotin. In this example 0.5 ml solution of 5 µM Test Probe 2 in PBS buffer is treated with streptavidin that has been pre-incubated with various levels (50, 100, 150, 200, 250, 300, 350, 400 ng and finally excess) of biotin and signal developed by addition of 0.375 mg of RSA (7.5 µl RSA 50 mg/ml solution) as the binder. An emission spectrum is recorded after each experiment using an excitation wavelength of 345 nm. Biotin concentration dependent increase in signal intensity is clearly evident as also shown in a plot (FIG. 14b) of intensity verses biotin concentration.

It is also to be noted that the fluorescence pyrene has been known to be sensitive to oxygen concentration (Biochem. Biophys. Acta 279 (1972) 393-397) as variations in fluorescence characteristics (intensity and lifetime) of pyrene result from dynamic quenching of pyrene by oxygen. Our assays may be improved using deoxygenated or argon purged solution to enhance the signal. It is also conceivable that the dependence of pyrene fluorescence on oxygen itself may be used to measure oxygen concentration using the probes of this invention whereby the FITC signal would report on oxygen levels when pyrene is excited.

In this example, we have shown the use of the popular highly fluorescent dye, fluorescein, as an emitter in combination with another donor fluorophore, such that excitation falls outside the background range and the emission of fluorescein exhibiting a very large Stokes shift. Quantitative emission in response to an analyte (biotin) has been demonstrated. While the measurements so far have relied on intensity measurements other techniques can also be used to follow fluorophore properties. Such techniques are commonly known and include, without limitation, life-time, time correlation, photon counting, multiphoton, polarization, quenching, FRET and photo induced electron transfer (PET). To substantiate this further FIG. 15a shows fluorescence decay profiles when the pyrene of test probe 2 was excited. Clearly the decay rates differ in the presence of RSA as the binder protein Gabelled as host) or in a test mixture where streptavidin is also included (FIG. 15b). Measurement of $\tau$ values and in particular their relative amplitudes with different levels of analyte could obviously be used to measure the analyte. For instance, in this particular experiment the amplitude of slower decay $\tau_2$ value showed significant variation. With all the assay components (test mix trace below)) present the decay rates changed further and most prominent values were $\tau_1=0.16$ nanosecond and $\tau_1=34$ nanosecond. Fluorescence intensity variation or fluorescence lifetime changes of pyrene derivatives are well documented (J. Photochem. Photobiol. B: Biol. 31 (1995) 145-158).

Many other variations and detection means of measuring analyte by fluorescence according to this invention are possible and such techniques when applied to probes of this invention are also considered to be within the scope of our claims.

Example 9

Highly Efficient Energy Transfer

To demonstrate extremely efficient transfer of energy, in the presence of a binder, from donor to acceptor a solution of test probe 2 was excited at the optimum wavelength of 345 nm for pyrene and optimum wavelength of 490 nm for FITC in the absence and presence of rabbit serum albumin (RSA) as the binder. FIG. 16 shows all four emission spectra. In this experiment 0.5 ml of 5 µM test probe 1 in PBS (phosphate buffered saline pH 7.4) is treated with 0.375 mg of RSA (7.51 µl RSA 50 mg/ml solution) as the binder. Emission spectrum is recorded by excitation at 345 nm and then at excitation of 490 nm. Spectra are also recorded before RSA treatment. It is clearly observed that the fluorescence intensity in the presence of RSA is higher when excitation is achieved via the donor compared to direct excitation of FITC while opposite is true in the absence of binder. The data in FIG. 16 indicates extremely high-energy transfer.

The invention claimed is:

1. A composition of at least two chemically different fluorophores, comprising a donor and an acceptor, the donor and acceptor connected together by at least one linker moiety and bonded to a binder moiety, wherein the binder moiety is a polypeptide structure defining a hydrophobic cavity.

2. A method of preparing a composition comprising the steps of linking two chemically different fluorophores together to form a unit, wherein the at least two chemically different fluorophores comprise a donor fluorophore and an acceptor fluorophore, and bonding a binder moiety to the unit, wherein the bonding of the binder moiety enhances the fluorescence intensity of the composition independently from any modification of an emission band of the donor fluorophore and an absorption band of the acceptor flourophore.

3. An assay method for assaying an analyte, the assay method comprising the steps of providing a composition linking two chemically different fluorophores together to form a unit, wherein the at least two chemically different fluorophores comprise a donor fluorophore and an acceptor fluorophore, and bonding a binder moiety to the unit, wherein the assay method further comprises the step of contacting the composition with a sample, and wherein the composition emits fluorescence in response to the presence of the analyte in the sample, wherein the fluorescence of the composition is reduced in response to the presence of the analyte in the sample.

* * * * *